US009167885B2

(12) United States Patent
Davis

(10) Patent No.: US 9,167,885 B2
(45) Date of Patent: Oct. 27, 2015

(54) AUTOMATIC SWITCHABLE LOW THRESHOLD CURRENT POWER SUPPLY

(71) Applicant: Murray W. Davis, Grosse Pointe Woods, MI (US)

(72) Inventor: Murray W. Davis, Grosse Pointe Woods, MI (US)

( * ) Notice: Subject to any disclaimer, the term of this patent is extended or adjusted under 35 U.S.C. 154(b) by 0 days.

(21) Appl. No.: 14/479,410

(22) Filed: Sep. 8, 2014

(65) Prior Publication Data

US 2014/0375302 A1    Dec. 25, 2014

Related U.S. Application Data

(62) Division of application No. 14/133,811, filed on Dec. 19, 2013, now Pat. No. 9,060,594.

(60) Provisional application No. 61/740,517, filed on Dec. 21, 2012.

(51) Int. Cl.

| | |
|---|---|
| *G01R 5/26* | (2006.01) |
| *A46B 9/02* | (2006.01) |
| *H02G 1/02* | (2006.01) |
| *G01B 11/06* | (2006.01) |
| *G01W 1/14* | (2006.01) |
| *G01R 1/20* | (2006.01) |
| *G01R 19/00* | (2006.01) |
| *G01R 31/08* | (2006.01) |
| *G01N 27/22* | (2006.01) |
| *H01F 38/30* | (2006.01) |

(Continued)

(52) U.S. Cl.
CPC ............ *A46B 9/028* (2013.01); *G01B 11/0616* (2013.01); *G01D 11/30* (2013.01); *G01K 13/00* (2013.01); *G01N 27/223* (2013.01); *G01R 1/20* (2013.01); *G01R 1/22* (2013.01); *G01R 19/0084* (2013.01); *G01R 19/0092* (2013.01); *G01R 31/08* (2013.01); *G01R 31/086* (2013.01); *G01R 31/40* (2013.01); *G01W 1/14* (2013.01); *H01F 27/02* (2013.01); *H01F 27/22* (2013.01); *H01F 38/30* (2013.01); *H01R 4/28* (2013.01); *H02G 1/02* (2013.01); *H04N 5/2252* (2013.01); *H04N 7/181* (2013.01); *A46B 2200/3073* (2013.01); *Y10T 29/49117* (2015.01)

(58) Field of Classification Search
None
See application file for complete search history.

(56) References Cited

U.S. PATENT DOCUMENTS

| | | |
|---|---|---|
| 2,004,998 A | 6/1935 | McCarty |
| 2,303,824 A | 12/1942 | Cornins |

(Continued)

FOREIGN PATENT DOCUMENTS

| | | |
|---|---|---|
| CN | 202041573 | 11/2011 |
| JP | 2003-061752 | 9/2004 |

OTHER PUBLICATIONS

Pradhan, et al., Fault Direction Estimation in Radial Distribution System Using Phase Change in Sequence Current, IEEE Transactions on Power Delivery, vol. 22, No. 4, pp. 2065-2071, Oct. 2007.

(Continued)

*Primary Examiner* — Paresh Patel
(74) *Attorney, Agent, or Firm* — Carlson, Gaskey & Olds, P.C.

(57) ABSTRACT

A method of operating a device connected to an electric power line conductor includes the steps of attaching a device to a first electric power line conductor, sensing a current in the first electric power line conductor and selecting between a first set of windings and a second set of windings connected in series with the first electric power line conductor.

18 Claims, 25 Drawing Sheets

(51) Int. Cl.

| | |
|---|---|
| H04N 5/225 | (2006.01) |
| G01D 11/30 | (2006.01) |
| G01K 13/00 | (2006.01) |
| H01F 27/02 | (2006.01) |
| H01F 27/22 | (2006.01) |
| H01R 4/28 | (2006.01) |
| G01R 1/22 | (2006.01) |
| G01R 31/40 | (2014.01) |
| H04N 7/18 | (2006.01) |

(56) References Cited

U.S. PATENT DOCUMENTS

| | | | |
|---|---|---|---|
| 2,306,117 | A | 12/1942 | Dunlap |
| 3,267,507 | A | 8/1966 | Cox |
| 3,622,867 | A | 11/1971 | Topper et al. |
| 3,678,372 | A * | 7/1972 | Elder ............... 323/342 |
| 3,764,891 | A * | 10/1973 | Lingenfelter et al. ...... 323/341 |
| 3,820,106 | A | 6/1974 | Yamashita et al. |
| 3,861,197 | A | 1/1975 | Adler |
| 4,032,842 | A | 6/1977 | Green et al. |
| 4,052,000 | A | 10/1977 | Honikman |
| 4,053,830 | A * | 10/1977 | Porter ............... 324/545 |
| 4,061,963 | A | 12/1977 | Green |
| 4,234,863 | A | 11/1980 | Shumway et al. |
| 4,242,930 | A | 1/1981 | Myers et al. |
| 4,268,818 | A | 5/1981 | Davis et al. |
| 4,326,316 | A | 4/1982 | Dolenti |
| 4,420,752 | A | 12/1983 | Davis et al. |
| 4,499,417 | A | 2/1985 | Wright et al. |
| 4,546,340 | A | 10/1985 | Kuchuris |
| 4,728,887 | A | 3/1988 | Davis |
| 4,746,241 | A | 5/1988 | Burbank |
| 4,801,937 | A | 1/1989 | Fernandes |
| 4,806,855 | A | 2/1989 | Davis |
| 4,827,272 | A | 5/1989 | Davis |
| 5,029,101 | A | 7/1991 | Fernandes |
| 5,140,257 | A | 8/1992 | Davis |
| 5,232,518 | A | 8/1993 | Nath et al. |
| 5,341,088 | A | 8/1994 | Davis |
| 5,351,359 | A | 10/1994 | Golden |
| 5,426,360 | A | 6/1995 | Maraio et al. |
| 5,703,568 | A | 12/1997 | Hegyi |
| 5,796,259 | A | 8/1998 | Dickmander |
| 5,883,511 | A | 3/1999 | Foster |
| 6,144,017 | A | 11/2000 | Millett et al. |
| 6,151,065 | A | 11/2000 | Steed et al. |
| 6,157,160 | A | 12/2000 | Okawa et al. |
| 6,299,824 | B1 | 10/2001 | Mayr et al. |
| 6,713,670 | B2 | 3/2004 | Stern et al. |
| 6,741,069 | B1 | 5/2004 | Klemar et al. |
| 6,924,732 | B2 | 8/2005 | Yokoo |
| 6,983,508 | B2 | 1/2006 | Saurer |
| 7,030,593 | B2 | 4/2006 | Pinkerton et al. |
| 7,127,972 | B2 | 10/2006 | Klein et al. |
| 7,310,109 | B2 | 12/2007 | Dottling et al. |
| 7,412,338 | B2 | 8/2008 | Wynans et al. |
| 7,432,787 | B2 | 10/2008 | Muench et al. |
| 7,545,140 | B2 | 6/2009 | Humphreys et al. |
| 7,557,563 | B2 | 7/2009 | Gunn et al. |
| 7,570,045 | B2 | 8/2009 | Wolfe et al. |
| 7,579,824 | B2 | 8/2009 | Rea |
| 7,706,596 | B2 | 4/2010 | Garvey |
| 8,022,291 | B2 | 9/2011 | Thomsen et al. |
| 8,144,445 | B2 | 3/2012 | Caggiano et al. |
| 8,184,015 | B2 | 5/2012 | Lilien et al. |
| 8,203,328 | B2 | 6/2012 | Bose et al. |
| 8,300,922 | B1 | 10/2012 | Garvey, III |
| 8,320,146 | B2 | 11/2012 | Haines et al. |
| 8,322,332 | B2 | 12/2012 | Rogers |
| 8,400,504 | B2 | 3/2013 | Al-Duwaish et al. |
| RE44,256 | E | 6/2013 | Bright et al. |
| 8,536,857 | B2 | 9/2013 | Nero, Jr. |
| 8,628,211 | B2 | 1/2014 | Jensen et al. |
| 8,686,302 | B2 | 4/2014 | Brasher et al. |
| 2003/0052687 | A1 | 3/2003 | McQueeney et al. |
| 2004/0012678 | A1 | 1/2004 | Li |
| 2006/0060007 | A1 | 3/2006 | Mekhanoshin |
| 2006/0125469 | A1 | 6/2006 | Hansen |
| 2008/0077336 | A1 | 3/2008 | Fernandes |
| 2008/0136403 | A1 | 6/2008 | Deck |
| 2008/0297162 | A1 | 12/2008 | Bright |
| 2009/0009180 | A1 | 1/2009 | Varghai et al. |
| 2009/0207421 | A1 | 8/2009 | Kelly et al. |
| 2009/0212241 | A1 | 8/2009 | McGeoch |
| 2009/0243876 | A1 | 10/2009 | Lilien et al. |
| 2010/0039090 | A1 * | 2/2010 | Sykes ............... 323/301 |
| 2010/0084920 | A1 | 4/2010 | Banting et al. |
| 2010/0085036 | A1 | 4/2010 | Banting et al. |
| 2010/0192975 | A1 | 8/2010 | Schweikert |
| 2011/0204879 | A1 | 8/2011 | Peretto |
| 2011/0267673 | A1 | 11/2011 | Agrawal et al. |
| 2011/0308566 | A1 | 12/2011 | Johnson |
| 2012/0086804 | A1 | 4/2012 | Ishibashi et al. |
| 2012/0152346 | A1 | 6/2012 | Yang et al. |
| 2013/0022078 | A1 | 1/2013 | Phillips et al. |
| 2013/0179079 | A1 | 7/2013 | Lancaster |
| 2013/0205900 | A1 | 8/2013 | Nulty |
| 2013/0221977 | A1 | 8/2013 | Ukil et al. |
| 2014/0110376 | A1 | 4/2014 | Zahlmann et al. |
| 2014/0123750 | A1 | 5/2014 | Liu et al. |
| 2014/0145858 | A1 | 5/2014 | Miller et al. |

OTHER PUBLICATIONS

Eissa, Evaluation of a New Current Directional Protection Technique Using Field Data, IEEE Transactions on Power Delivery, vol. 20, No. 2, pp. 566-572, Apr. 2005.

Ukil, et al., Smart Distribution Protection Using Current-Only Directional Overcurrent Relay, Innovative Smart Grid Technologies Conference Europe, 2010 IEEE PES, pp. 1-7, 2010.

Recloser, available at http://en.wikipedia.org/wiki/Recloser on Feb. 2, 2012.

Digital protective relay, available at http://en.wikipedia.org/wiki/Digital_protective_relay on Jun. 18, 2012.

* cited by examiner

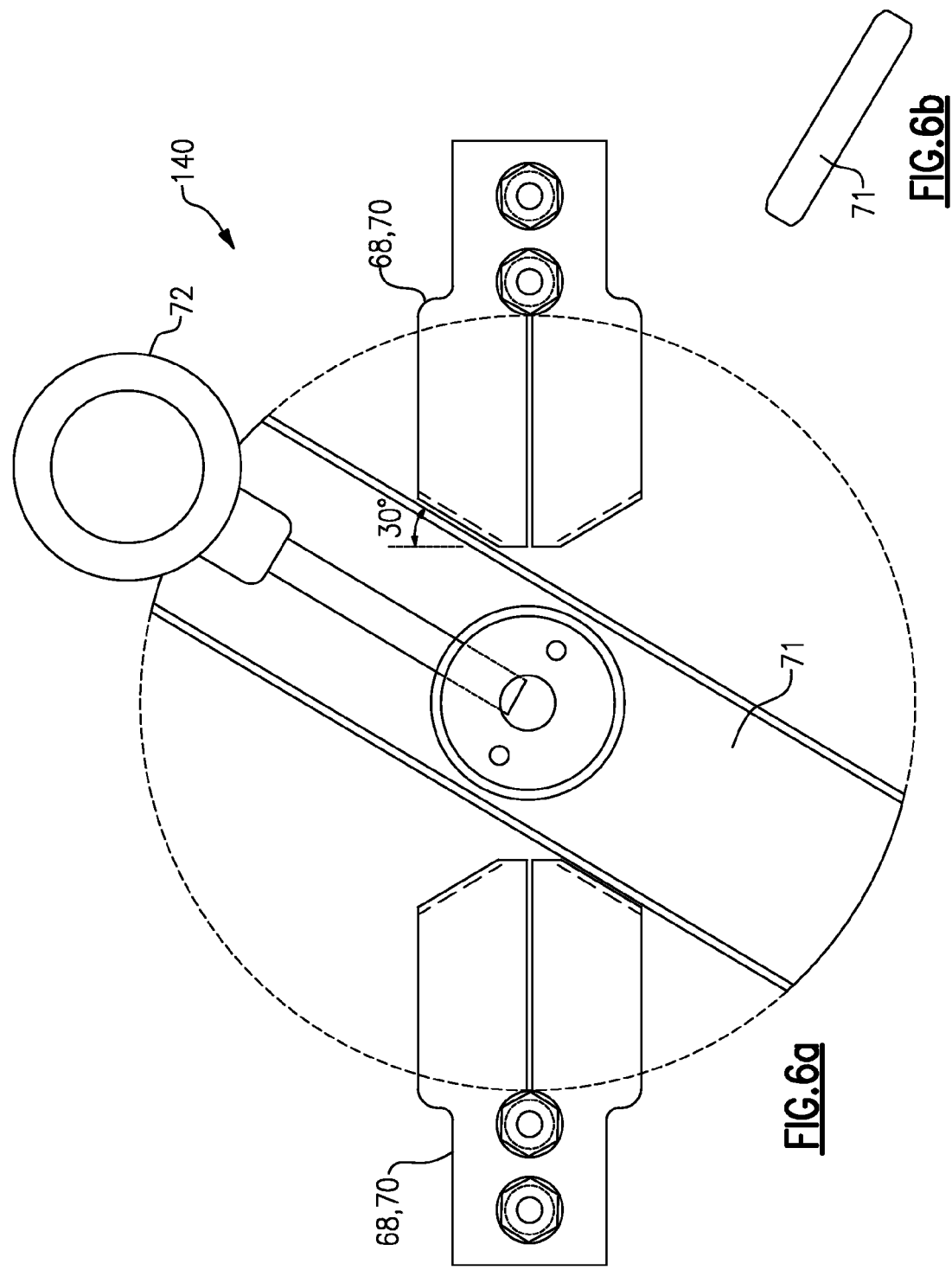

AUTOMATIC SWITCHABLE LOW THRESHOLD CURRENT POWER SUPPLY

CROSS-REFERENCE TO RELATED APPLICATIONS

The application is a divisional of U.S. application Ser. No. 14/133,811 filed Dec. 19, 2013 which claims priority to U.S. Provisional Application No. 61/740,517 which was filed on Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device which is low maintenance and can be constantly powered independent of weather conditions over a wide range of current flowing in the power line conductor using an automatic switchable low threshold current power supply.

SUMMARY

In one exemplary embodiment, a method of operating a device connected to an electric power line conductor includes the steps of attaching a device to an electric power line conductor, sensing a current in an electric power line conductor and selecting between a first set of windings and a second set of windings connected in series with the electric power line conductor.

These and other features of the disclosed examples can be understood from the following description and the accompanying drawings, which can be briefly described as follows.

BRIEF DESCRIPTION OF THE DRAWINGS

FIG. 6a schematically illustrates the rotary by-pass switch blade contacting the by-pass contact fingers at 30 degrees.

FIG. 6b illustrates an end of the rotary by-pass switch blade with rounded corners.

FIG. 14b illustrates an enlarged view of Detail "D" of FIG. 14a.

FIG. 14c illustrates an enlarged view of Detail "E" of FIG. 14a.

DETAILED DESCRIPTION

Figure 1:
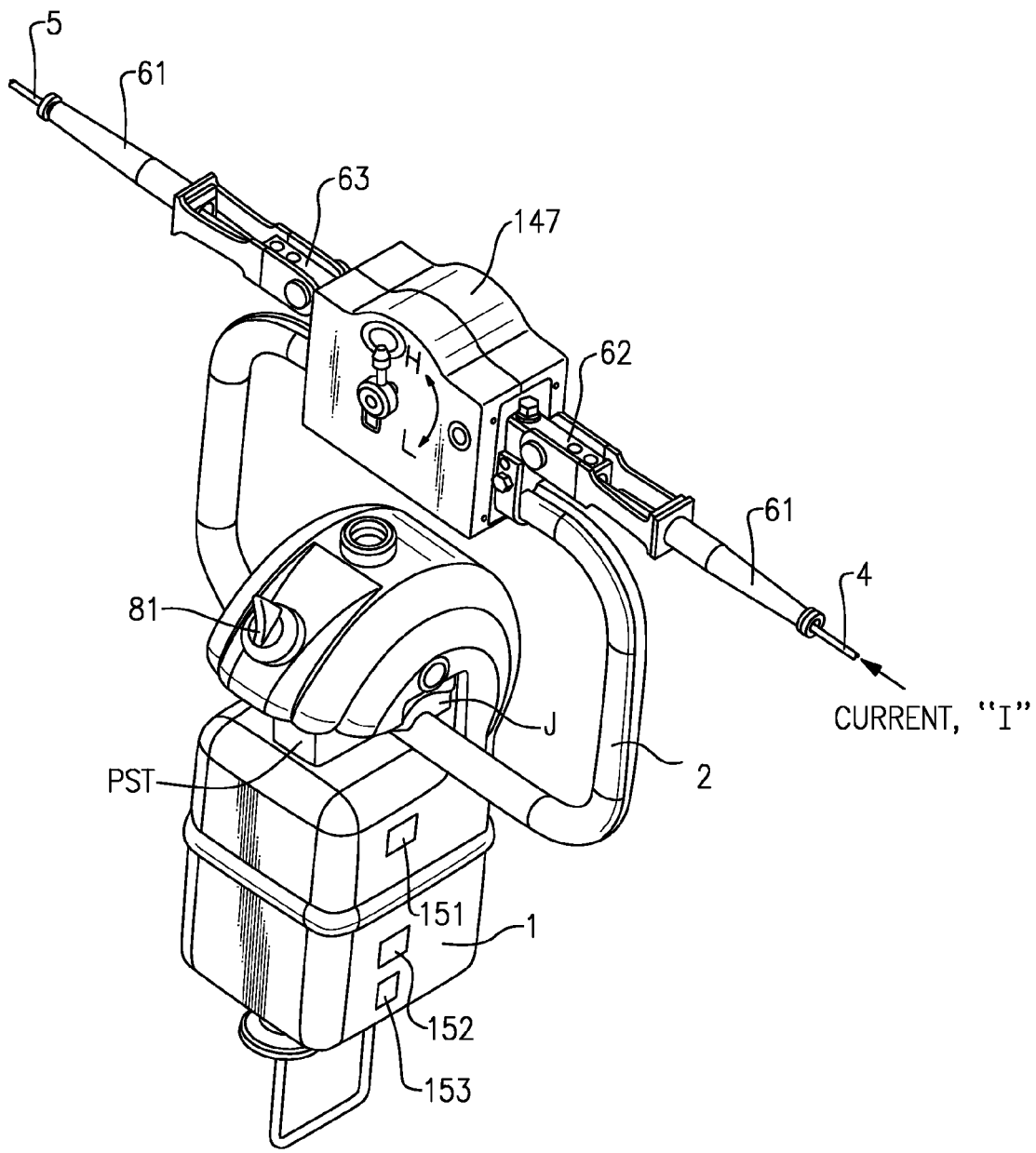
FIG. 1 illustrates a STR unit mounted on a switchable low threshold current power supply ("LTPS").

FIG. 1 illustrates a switchable low threshold current power supply (LTPS) 147 attached to a conductor 4 and a conductor 5. A loop tube 2 extends from the switchable LTPS 147 for mounting an example sensor transmitter receiver unit ("STR unit") 1.

The STR unit 1 includes an iron core power supply transformer PST that surrounds the loop tube 2 when a pair of jaws J is clamped onto the loop tube 2.

Without the switchable LTPS 147, a fixed tap LTPS with five turns of wire is limited to a maximum of 29.4 times (i.e., 1000/(6.8 amps×5 turns)), that is the STR unit 1 will operate down to 6.8 amperes of power line current and as high as 200 amperes. The high limit is 200 amperes because five turns times 200 amperes results in 1000 amperes as seen by the STR unit 1 which is the maximum rating for the STR unit 1.

This range can be increased dramatically with the switchable LTPS 147. For example, if five turns were selected for low power line currents and two turns were selected for high power line currents, then the dynamic range is extended. For two turns, the lowest threshold current needed for the STR unit 1 to operate and transmit data at full power is 17 amperes (i.e., 17 amperes×2 turns equals 34 amperes) which coincides with the lowest current the STR unit 1 will operate without the switchable LTPS 147. But, the highest current without exceeding the rating of the STR unit 1 for two turns is 366 amperes. Since 366 amperes times 2 turns is 732 amperes, this is below the 1000 ampere rating of the STR unit 1. With a switchable tap selector switching from five turns to two turns, then the dynamic range for the STR unit 1 is now from 6.8 amperes of power line current and up to 366 amperes. The dynamic range of 53.8 times or (366 A÷6.8 A=53.8), is 1.83 times (i.e. 53.8 times÷29.4 times=1.83) the range for a fixed tap five turn low threshold current power supply.

One problem that could be encountered by some electric power utilities is they might not know the range of power line currents on each single phase lateral in their system. For example, if they were to select a five turn fixed tap LTPS and the STR unit 1 operates successfully down to the low threshold of 6.8 amperes, but the lateral current may actually rise above 200 amperes, then the rating of the STR unit 1 would sometime during the year, be exceeded. If they were to select a 4 turn fixed tap LTPS, the lateral current could be as high as 250 amperes, but the lowest lateral current the STR unit 1 will operate down to is now 8.5 amperes. So rather than purchase four LTPS units with individual five turn, four turn, three turn, and two turn fixed tap LTPS windings, the switchable LTPS 147 could be used to switch from five turns to two turns. Then the full range of lateral currents from a low of 6.8 amperes and up to a high of 366 amperes could be satisfied with one switchable LTPS 147.

With the switchable LTPS 147, the separate windings do not have to be the same size. For example, the two turn winding of wire 6 could be made a larger conductor size than the five turn winding of wire 6. With the two turn winding of wire 6 made of 1/0 copper wire, the power line current can be increased to 413 amperes, while not exceeding the rating of the STR unit 1, because the 413 amperes times two turns is equal to 826 amperes which is below the 1000 ampere rating for the STR unit 1. With the use of 1/0 copper two turn winding of wire 6, now the dynamic range is 6.8 amperes to 413 amperes which is 60.7 times or 2.07 bigger (i.e. 60.7×÷29.4×=2.07) than if the two turn and the five turn windings of wire 6 were the same wire size.

If the SØ lateral current were to drop below 6.8 amperes, then an additional turn of wire can easily be added to the design described above, in which case the new lower threshold current would be (i.e. 34 A÷6 turns=5.7 A) 5.7 amperes. The high end ampere limit is now reduced to 166.7 amperes, since 166.7 A×6 turns=1000 A. In cases where even lower threshold currents exist, the wire size can be reduced to allow even more turns than the six mentioned above to be added within the same space inside the loop tube 2 of FIG. 1. With the smaller wire size the maximum current allowed in the winding of wire 6 would also be reduced.

Figure 2:
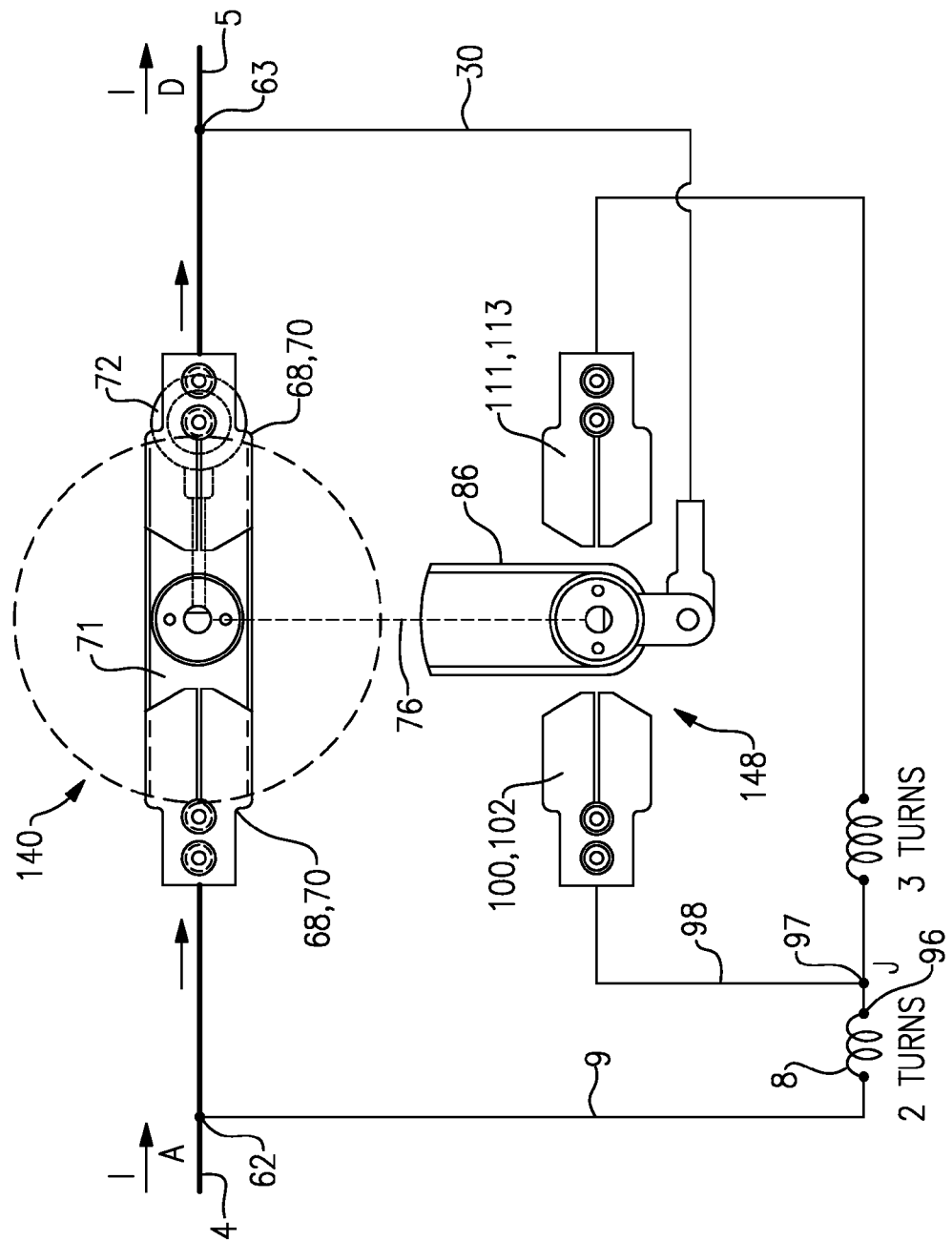
FIG. 2 schematically illustrates the switchable LTPS with a by-pass switch in a closed position and a tap selector switch in an open position.

FIG. 2 illustrates a by-pass switch 140 in a "closed" position. Node "A" represents the left anchor rod 62 and node "D" represents the right anchor rod 63 of FIG. 1. The current I flows from the conductor 4 to the conductor 5. The by-pass switch 140 which is shown in the horizontal position, allows the power line current to flow from the conductor 4 to the conductor 5 when a rotary by-pass switch blade 71 is in contact with the contact fingers 68, 70 on the left and with the contact fingers 68, 70 on the right. In the lower portion of FIG. 2, a rotary tap selector blade 86 is shown "open". In this case, all the current flows from the conductor 4 to the conductor 5 through the by-pass switch 140. It should be noted all contact fingers exist in pairs, that is 68, 70; 100, 102; and 111, 113.

The rotary tap selector blade 86 is connected to the by-pass switch blade through a common connection shaft 76 which has an operator handle 72. Therefore, when the by-pass switch blade is closed, or horizontal, and the operator handle 72 is in the horizontal position on the right, the tap selector switch blade 86 is vertical or "open". The left anchor rod 62 is electrically connected not only to left by-pass switch left contact fingers 68 and 70, but also to a connector 9 which in turn is connected to the beginning of a first two turn winding 8 of wire 6 of FIG. 2. After completing the two windings of wire 6, the end turn 96 of the two turn windings of wire 6 is connected to a "tee tap" 97 which forms a junction "J".

Figure 3:
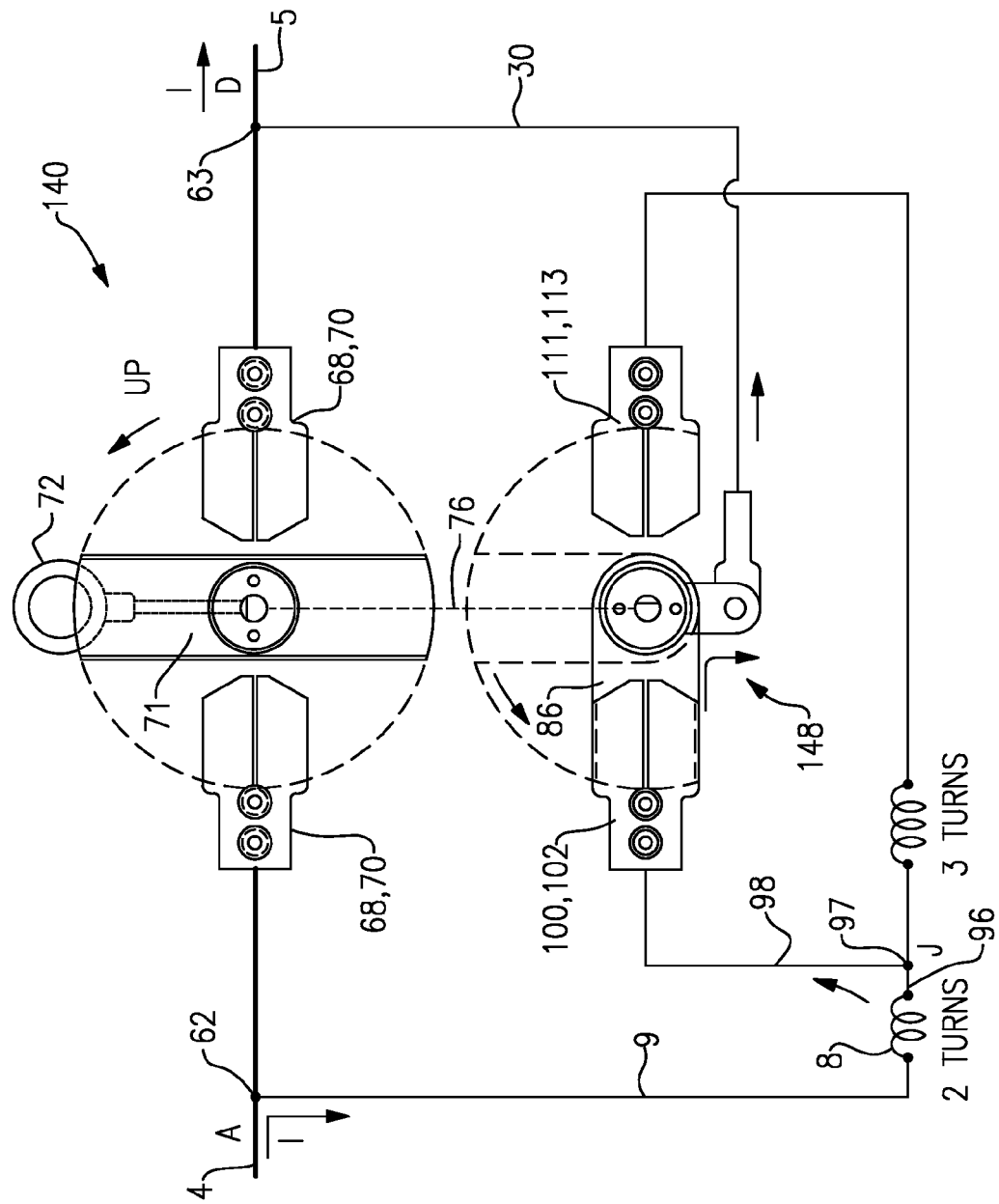
FIG. 3 schematically illustrates the switchable LTPS with a by-pass switch in an open position and a tap selector switch in closed high threshold current position.

Referring to FIG. 3, the operator handle 72 is pulled "up" which rotates the connection shaft 76 counterclockwise 90°. The rotary by-pass switch blade 71 is now vertical or "open" and the rotary tap selector blade 86 is now in full electrical contact with left tap selector contact fingers 100 and 102 which forms a current path from "J" through the rotary tap selector blade 86 and then onto a connector 30 of FIG. 3 and back to the right anchor rod 63 and the conductor 5. The tap selector switch 148 in the position shown in FIG. 3 represents the "high" threshold current, because the two windings of wire 6 provide a threshold current of 17 amperes.

Figure 4:
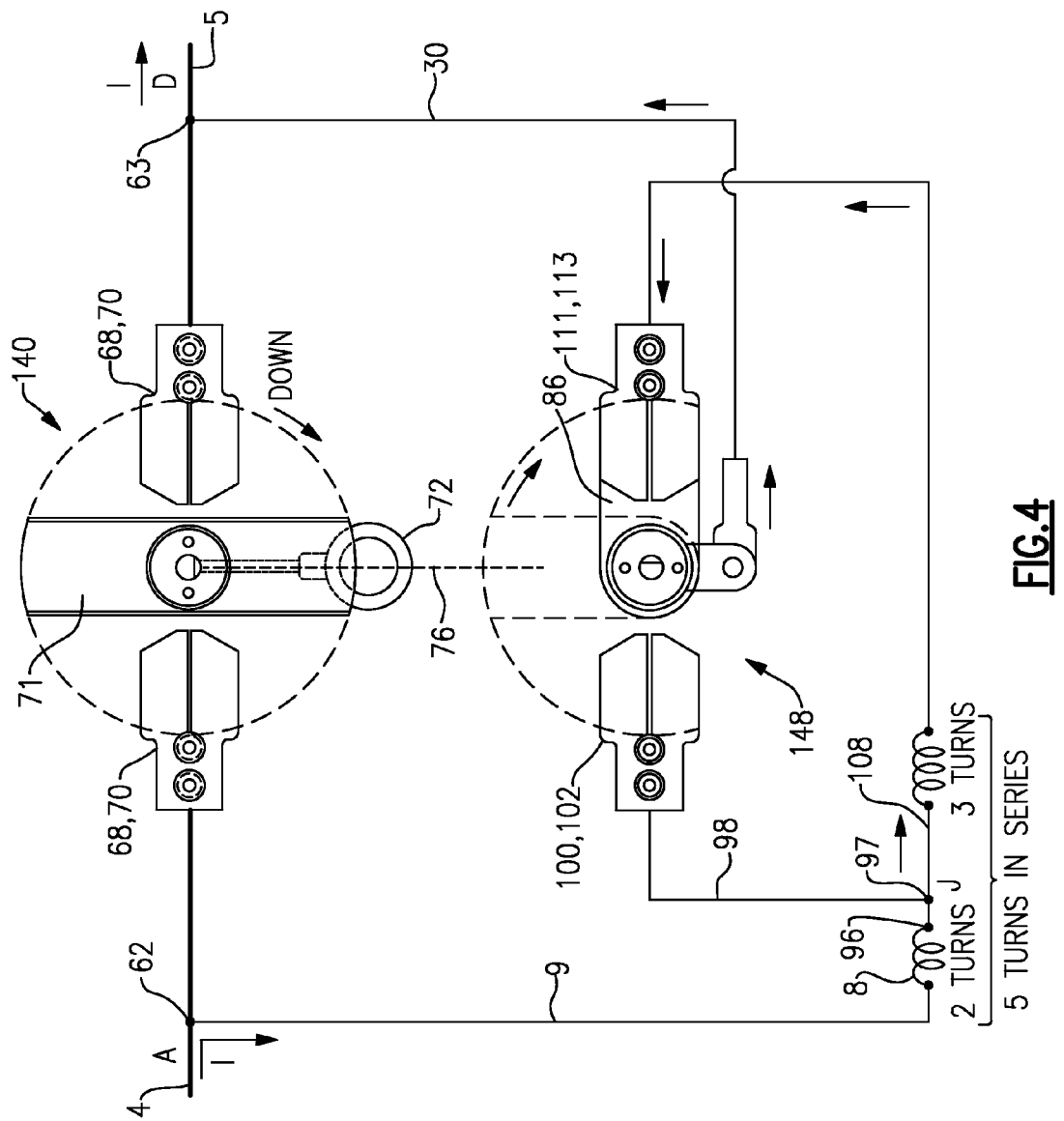
FIG. 4 schematically illustrates the switchable LTPS with a by-pass switch in an open position and a tap selector switch in closed low threshold current position.

In FIG. 4, the operator handle 72 is pulled "down" rotating the rotary by-pass switch blade 71 180° clockwise from FIG. 3. The rotary tap selector blade 86 is now in full electrical contact with the right tap selector contact fingers 111 and 113. The power line current from the conductor 4 flows through the two turns and three turns in series for a total of five turns. Then the current flows through the right tap selector contact fingers 111 and 113, the rotary tap selector blade 86, the connector 30, the right anchor rod 63, and the conductor 5. The tap selector switch 148 in the position shown in FIG. 4 represents the low threshold current when the winding of wire 6 have five turns and the threshold current is 6.8 amperes.

Figure 5:
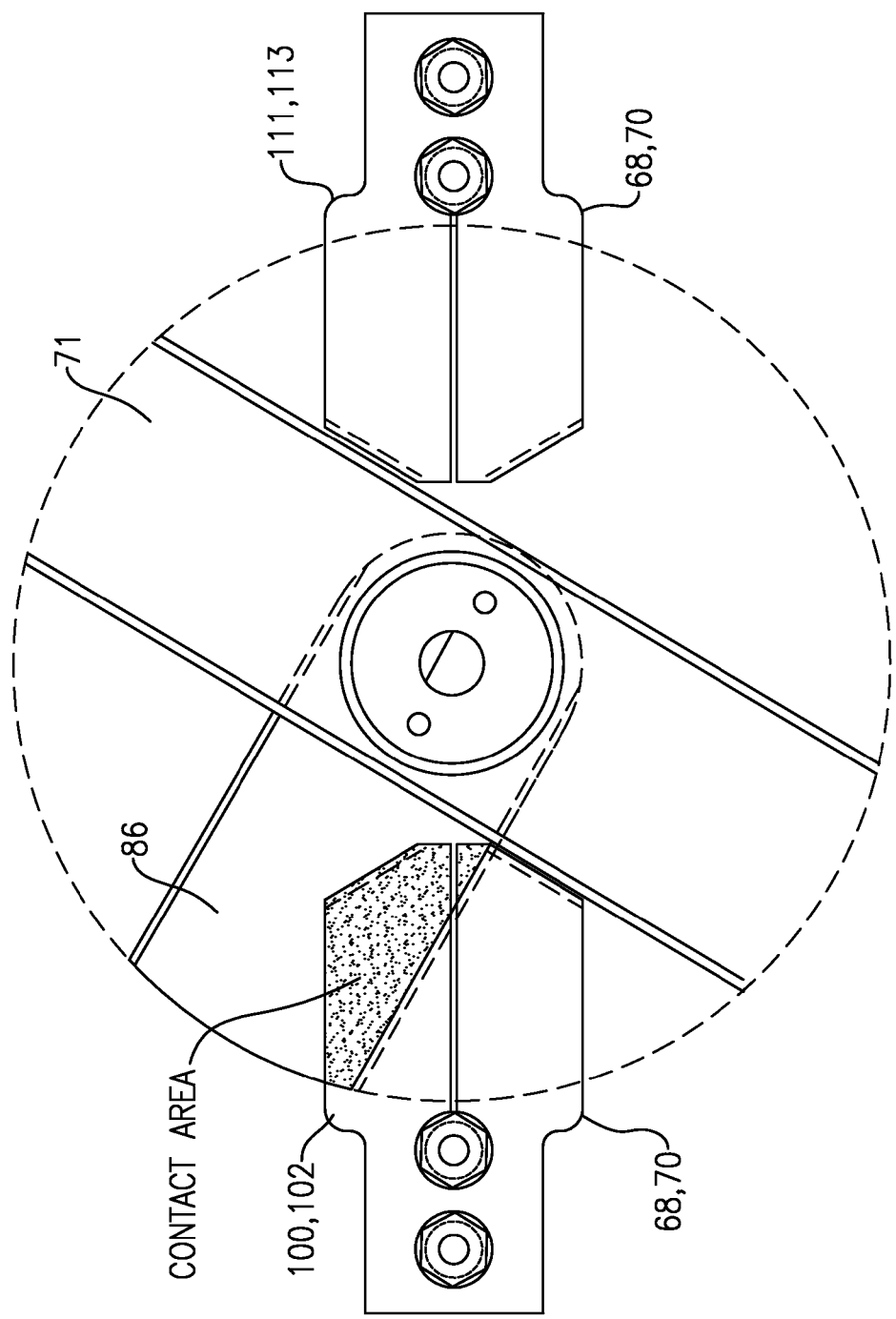
FIG. 5 schematically illustrates the rotary by-pass switch blade imposed over the rotary tap selector blade showing a 38.3% overlap with the rotary tap selector blade and tap selector fingers when the rotary by-pass switch blade is disengaged from by-pass contact fingers.
Figure 19:
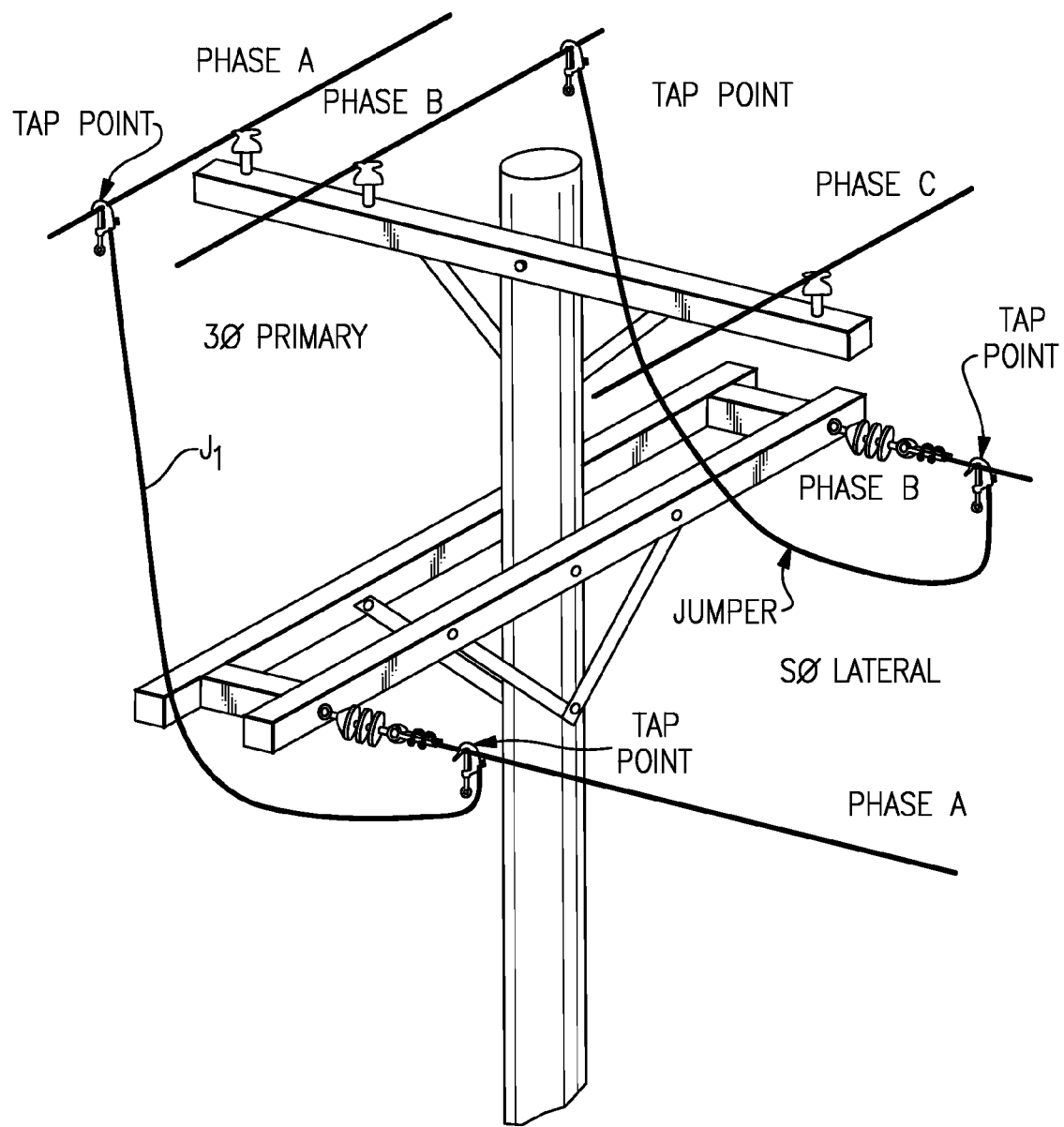
FIG. 19 illustrates tap points of a single phase lateral off of phases "A" and "B" of the three phase primary for a delta connected electric power system.

The switchable LTPS 147 must provide continuous electrical service to the customers served by the SØ lateral shown in FIG. 19 no matter where the by-pass switch 140 and the tap selector switch 148 may be permanently positioned as well as during the switching operation itself. The switchable LTPS 147 must provide continuous electrical service during switching operations when the rotary by-pass switch blade 71 is between the by-pass switch contact fingers 68 and 70 and the rotary by-pass switch blade 71 is between the left tap selector contact fingers 100 and 102 and the right tap selector contact fingers 111 and 113 as shown in FIG. 5. To insure continuous electrical service, the rotary by-pass switch blade 71 is mounted at right angles to the rotary tap selector blade 86.

As noted in FIG. 5, there is always an overlap of 38.3% of the rotary tap selector blade 86 with the left tap selector contact fingers 100 and 102 and the right tap selector contact fingers 111 and 113 at the moment the rotary by-pass switch blade 71 clears the by-pass switch contact fingers 68 and 70.

FIG. 5 illustrates the rotary by-pass switch blade 71 at the moment it clears the by-pass switch contact fingers 68 and 70 having a 38.3% overlap of surface area between the by-pass switch contact fingers 68 and 70 with the rotary by-pass switch blade 71. With this arrangement of blades 71 and 86 and contact fingers 68, 70, 100, 102, 111, and 113 for the by-pass switch 140 and the tap selector switch 148 there can never be a switching position where power line current is not flowing through either the by-pass switch 140 or the tap selector switch 148. However, the operator handle 72 must always be in the "closed" position for the by-pass switch, if the loop tube 2 and the winding of wire 6 are removed from the left and right anchor rods 62 and 63 by removing the nuts 17 from the threaded studs 13 of FIGS. 8 and 10.

FIG. 6*a* illustrates that the by-pass switch contact fingers 68 and 70 of the by-pass switch 140 have a 30° angle cut on the top and bottom of the by-pass switch contact fingers 68 and 70 and are rounded on the inside edge of each finger at the 30° cut line. The purpose of the angle and the rounded inside edge is to reduce the wear on the by-pass switch contact fingers 68 and 70 and reduce the wear on the rotary by-pass switch blade 71. Had the ends of the by-pass switch contact fingers 68 and 70 been square, then a very sharp point of contact between the by-pass switch contact fingers 68 and 70 and the rotary by-pass switch blade 71 would occur. The same 30 degree angle and rounded inside edge are used on the left and right tap selector contact fingers 100, 102, 111, and 113. The rotary by-pass switch blade 71 also includes rounded edges as shown in FIG. 6*b*.

Figure 8:
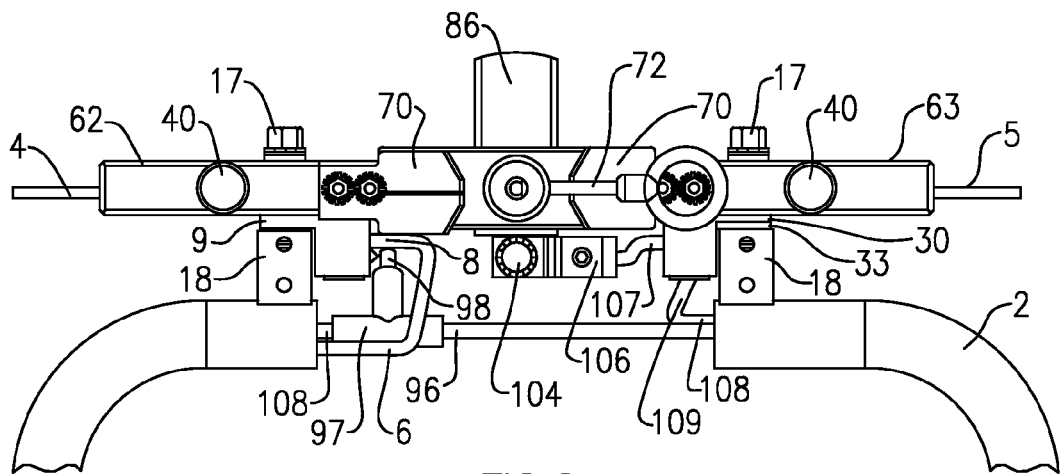
FIG. 8 illustrates an enlarged view of Detail "C" of FIG. 7.
Figure 7:
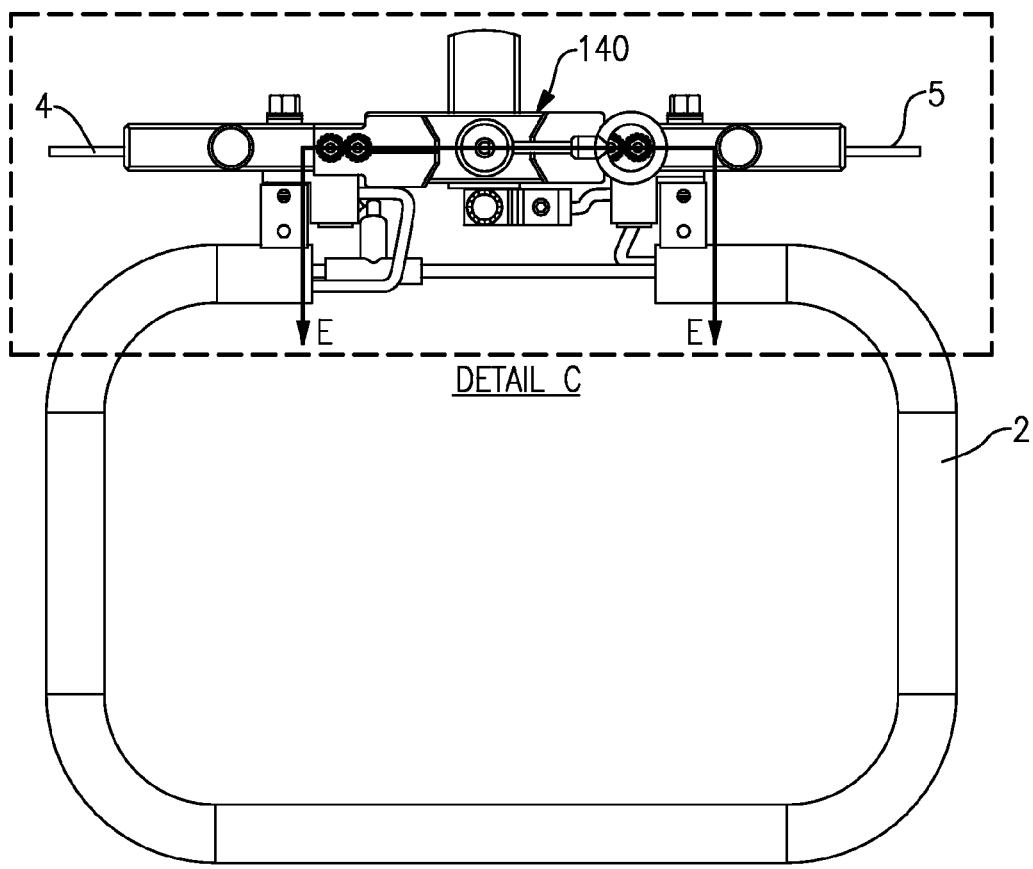
FIG. 7 illustrates a front view of the by-pass switch shown in the closed position and the tap selector switch shown in the open position.
Figure 9:
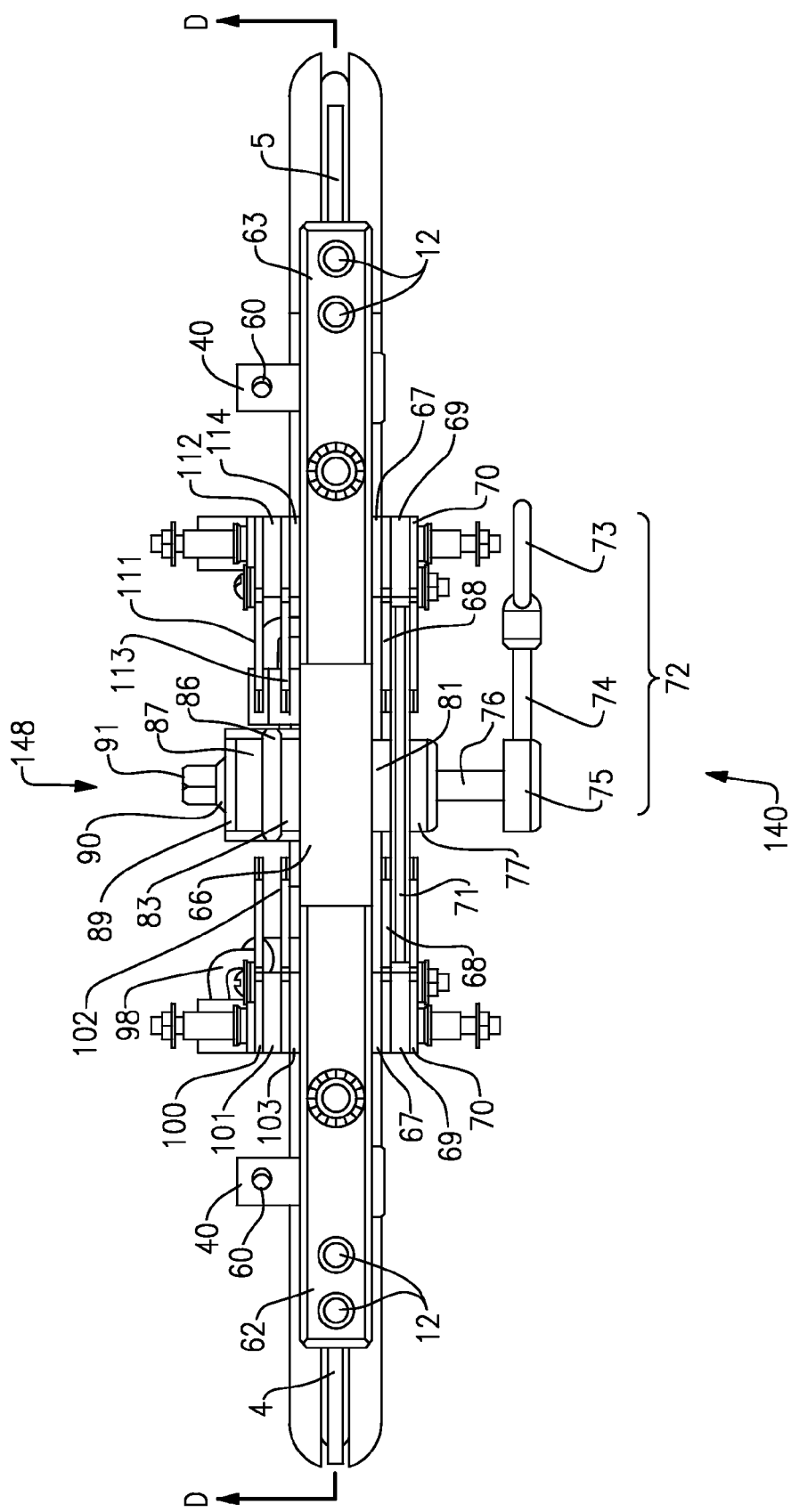
FIG. 9 illustrates a top view of the by-pass switch shown in the closed position and the tap selector switch shown in the open position.

Referring to FIGS. 7-9, it is imperative that the vertical height of by-pass switch 140 and the tap selector switch 148 be as short as possible to prevent electrical contact with the 3Ø primary phase conductors above as seen in the installation drawings of 20 and 21, when the operator handle 72 is moved "up" or "down" by a lineman. Furthermore, the bottom of the rotary by-pass switch blade 71 and the rotary tap selector blade 86 must be made as short as possible to prevent interfering with the STR unit 1 hung on the bottom of the loop tube 2 of FIG. 1. Conventional knife switches are available as commercial products, but are totally unsuitable for this application, because the blades with a 200 ampere or 350 ampere rating in the open position are over 12 inches tall. The rotary blade concept here results in blade heights and depths of only 2.5 inches measured from the centerline of their rotating axis to the tip of their blades.

Referring again to FIGS. 7-9, it is apparent the by-pass switch 140 is in front and the tap selector switch 148 is in the back and the switches are interconnected with the left and right anchor rods 62 and 63 of FIG. 8. The left and right anchor rods 62 and 63 are held together with two threaded studs 64 and 65 shown in FIG. 10. The threaded stud 64 is threaded into the left anchor rod 62 on the left and into an electrically insulating spacer rod 66 on the right. The threaded stud 65 is threaded into an electrically insulating spacer rod 66 on the left and into the right anchor rod 63 on the right. The two threaded studs 64 and 65 do not touch each other in the center of the spacer rod 66. Therefore the power line current cannot flow from the left anchor rod 62 to the right anchor rod 63, except when the by-pass switch 140 is closed or the tap selector switch 148 is closed.

When the by-pass switch is closed as in FIGS. 7-9, the power line current flows from the conductor 4 on the left, through the electrically conducting left anchor rod 62, through an electrically conducting spacer 67, an electrically conducting left back by-pass switch contact finger 68, and through an electrically conducting finger spacer 69, a front by-pass switch contact finger 70 and onto the rotary by-pass switch blade 71. It should be noted the current splits in half, one half through the back by-pass switch contact finger 68 and onto the rotary by-pass switch blade 71, and the other half through the electrically conducting spacer 69, through the front by-pass switch contact finger 70 and onto the rotary by-pass switch blade 71. As such the back and front by-pass switch contact fingers 68 and 70 are rated for one half the current magnitude and the rotary by-pass switch blade 71 is rated for the full current magnitude. The current then flows through the rotary by-pass switch blade 71 from left to right and again splits in half with one half flowing through the back by-pass switch contact finger 68 on the right and spacer 67 on the right and the other half flowing through the front by-pass switch contact finger 70, the electrically conducting finger spacer 69 and the spacer 67. The parts, spacer 67, the back by-pass contact finger 68, the finger spacer 69, and the front by-pass switch contact finger 70 on the right are identical to the same parts on the left.

From the spacer 67, the current then flows through the electrically conducting right anchor rod 63 on the right and onto the electric power line conductor 5 on the right. Two set screws 12 of FIG. 9 on each end of the left and right anchor rods 62 and 63 are used to clamp the conductors 4 and 5 to the respective left and right anchor rods 62 and 63.

Figure 11:
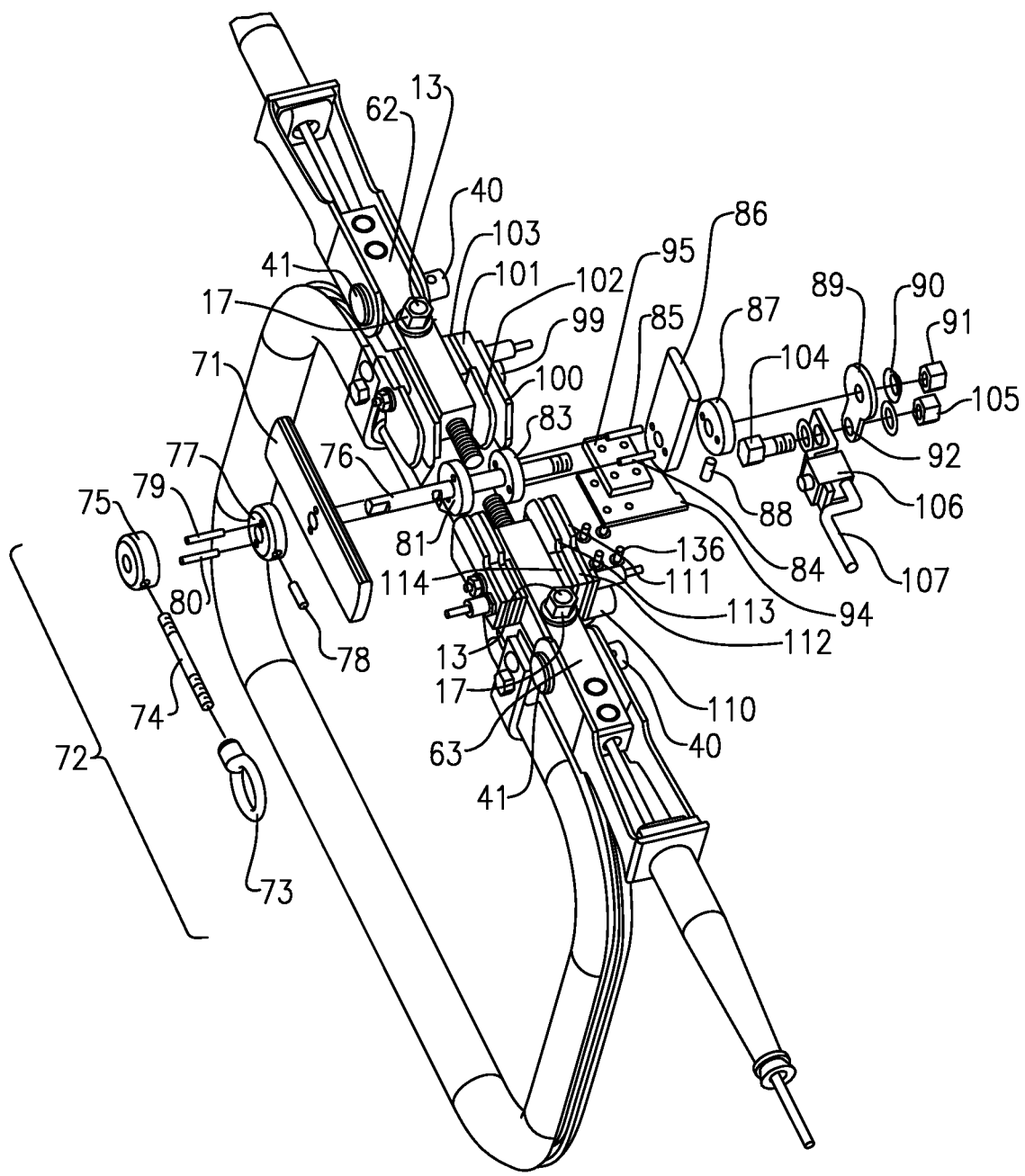
FIG. 11 illustrates an exploded view of an operator handle and associated parts of switchable low threshold current power supply.

As shown in FIG. 2, the operator handle 72 which is also shown in FIGS. 7-9 is used by the lineman to operate the by-pass switch and the tap selector switch with one operation since the two switches are ganged together by a connection shaft 76. The operator handle 72 and its associated parts are shown in FIG. 11. When the operator handle 72 is in the horizontal position and an operator handle ring 73 points to the right, the rotary by-pass switch blade 71 is closed and is in the horizontal position as shown in FIG. 2.

The operator handle ring 73 of FIG. 11 has a large hole through which a lineman inserts an electrically insulated hot stick called a "J" hook. The lineman can operate the switch while the electric power line is energized and can open the by-pass switch 140 by pushing the operator handle 72 "up", which as shown in FIG. 3 closes the rotary tap selector blade 86 against the left tap selector contact fingers 100 and 102 on the tap selector switch 148.

The lineman can pull the operator handle 72 "down" as shown in FIG. 4 and closes the rotary tap selector blade 86 against the right tap selector contact fingers 111 and 113 on the tap selector switch 148. The operator handle 72 includes the operator handle ring 73, an operator handle shaft 74, and an operator handle hub 75 as shown in FIG. 11. The operator handle shaft 74 is screwed into the operator handle hub 75 until it rests on a flat of the connection shaft 76. The connection shaft 76 is connected to the rotary by-pass switch blade 71 through the use of a by-pass switch hub 77 and with a set screw 78 that securely fastens the hub 77 to the flat on the connection shaft 76 and has the same orientation on the flat of the connection shaft 76 where the operator handle shaft 74 rests. The orientation of flats on the connection shaft 76 insures the operator handle 72 has the same position as the rotary by-pass switch blade 71.

The rotary by-pass switch blade 71 is attached to the hub 77 with the use of two dowel pins 79 ad 80 which are pressed into two holes in the hub 77, through the two holes in the rotary by-pass switch blade 71, and through the two holes in the rotating bushing 81 behind the rotary by-pass switch blade

71. Since the rotary by-pass switch blade 71 is sandwiched between the hub 77 and the bushing 81 and the hub 77 is firmly fixed to the connection shaft 76, then the rotary by-pass switch blade 71 will always strike precisely between the by-pass switch contact fingers 68 and 70 on the left and right as indicated in FIG. 9.

Figure 10:
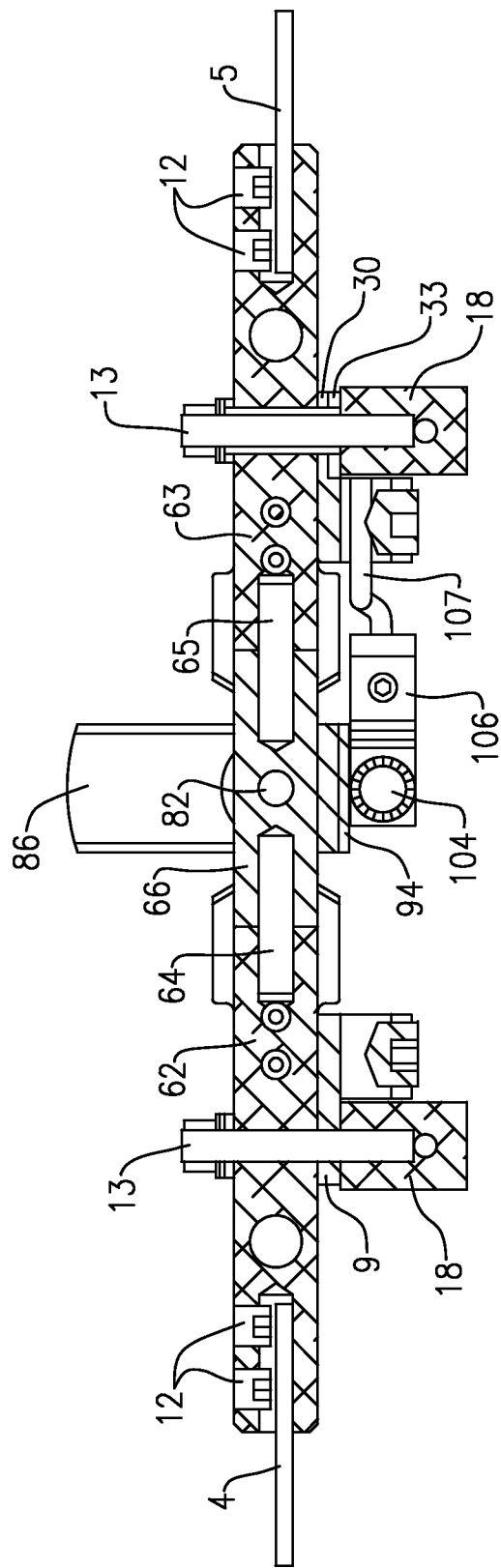
FIG. 10 illustrates a cross-sectional view taken along line D-D of FIG. 9.

The connection shaft 76 extends through a hole 82 which is centered vertically and horizontally in the spacer rod 66 shown in FIG. 10. The connection shaft 76 continues to the back side of the spacer rod 66 where the rotary tap selector blade 86 is fixed to the connection shaft 76 using a similar arrangement as was described for the rotary by-pass switch blade 71. Here a rotating bushing 83, the rotary tap selector blade 86 and a tap selector rotating contact 87 are held together as a unit with the dowel pins 84 and 85 and the tap selector rotating contact 87 is held firmly to the connection shaft 76 with a set screw 88 on the bottom. The set screw 88 is screwed into the flat of the connection shaft 76 that is located clockwise 90 degrees from the set screw 78. Therefore the rotary tap selector blade 86 will always be positioned "up" when the by-pass blade is horizontal. This arrangement insures that the rotary tap selector blade 86 will always enter precisely between the two sets of contact fingers 100, 102, 111, and 113 which results in an equal sharing of current from the rotary tap selector blade 86 to its contact fingers.

Again, referring to FIG. 11, the end of the connection shaft 76 includes a stationary disc contact 89 which is firmly held against the tap selector rotating contact 87 with a Belleville washer 90 and a lock nut 91. The lock nut 91 is adjusted so the Belleville washer 90 provides the proper pressure against the stationary disc contact 89 and the tap selector rotating contact 87.

Figure 12:
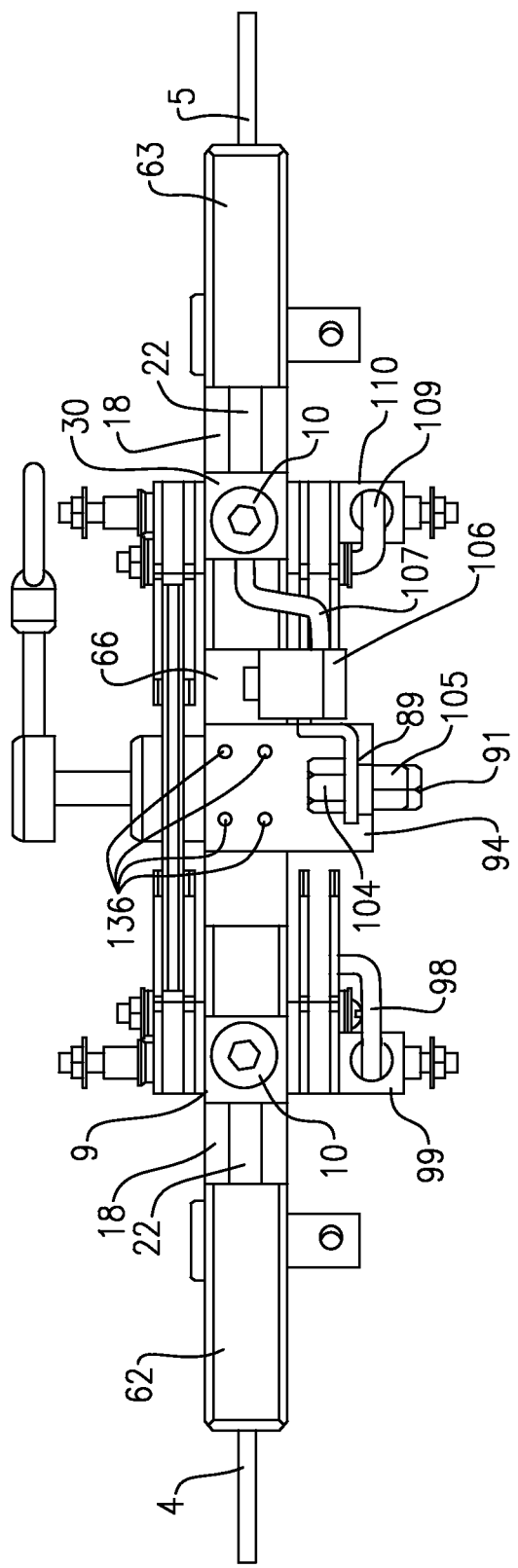
FIG. 12 illustrates a bottom view of the by-pass switch shown in the closed position and the tap selector switch shown in the open position.

As will be described next, current flows from the left tap selector contact fingers 100 and 102 through the rotary tap selector blade 86 to the tap selector rotating contact 87 to the stationary disc contact 89. The stationary disc contact 89 has a hole 92 in a center through which the connection shaft 76 fits through and a hole 93 at the bottom where an electrical offset connector 106 is attached thereto. The stationary disc contact 89 is prevented from rotating with the use of a keeper stop 94, which is mounted underneath the spacer rod 66 and has two projections one on either side which straddles the lower lobe of the stationary disc contact 89. The keeper stop 94 is mounted with four screws 136 threaded into the spacer rod 66 as shown in FIG. 12. Also, the keeper stop 94 includes a spacer 95 that prevents the rotary tap selector blade 86 from rotating beyond its horizontal positions.

Figure 13:
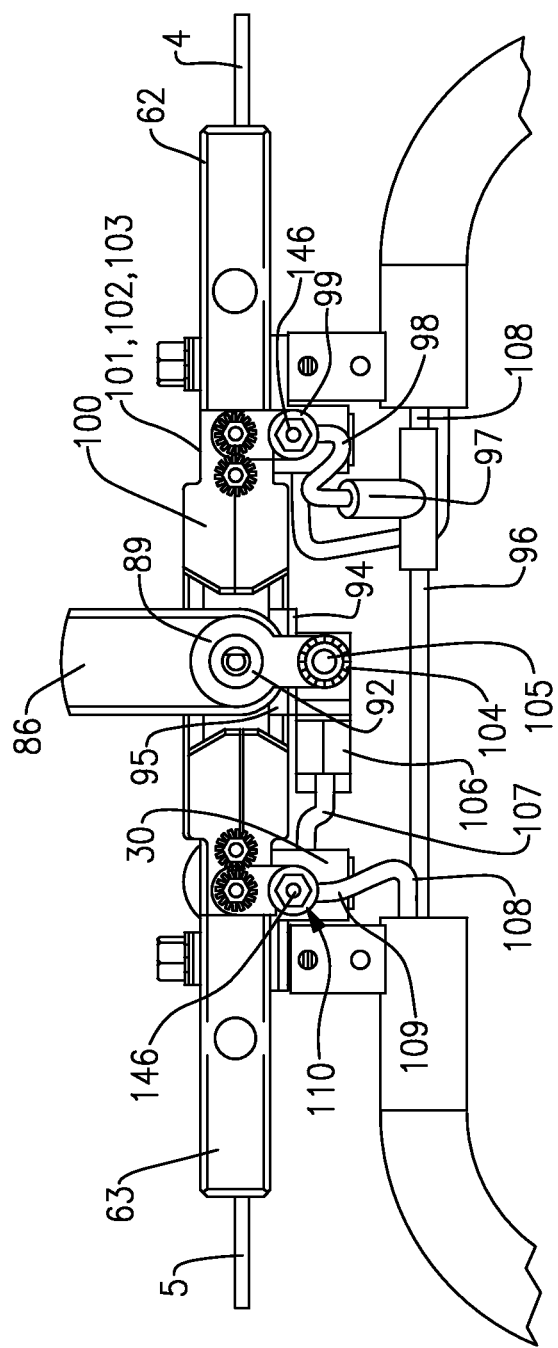
FIG. 13 illustrates a back view of the by-pass switch shown in the closed position and the tap selector switch shown in the open position.

Referring again to FIG. 3, when the operating handle 72 is pushed "up" to the vertical position, the rotary tap selector blade 86 is fully engaged with the left tap selector contact fingers 100 and 102 and the by-pass switch 140 is open. In this position, the power line current flows from the conductor 4 of FIG. 8 to the beginning of the first turn 8 of the winding of wire 6 and after two turns through the loop tube 2 an end turn 96 of the winding of wire 6 enters the "tee tap" 97. A wire lead 98 out of the top of the "tee tap" 97 is connected to a wiring connector 99 as shown in FIGS. 12 and 13.

Referring to FIG. 11, the current then splits in half, with one half flowing through the left front tap selector contact finger 100 and the other half flowing through the electrically conducting finger spacer 101 and the left back tap selector contact finger 102. The current is prevented from flowing into the left anchor rod 62, because the left tap selector contact fingers 100 and 102 and the finger spacer 101 are electrically insulated by an insulating spacer 103 between the left back tap selector contact finger 102 and the left anchor rod 62.

Figure 23:
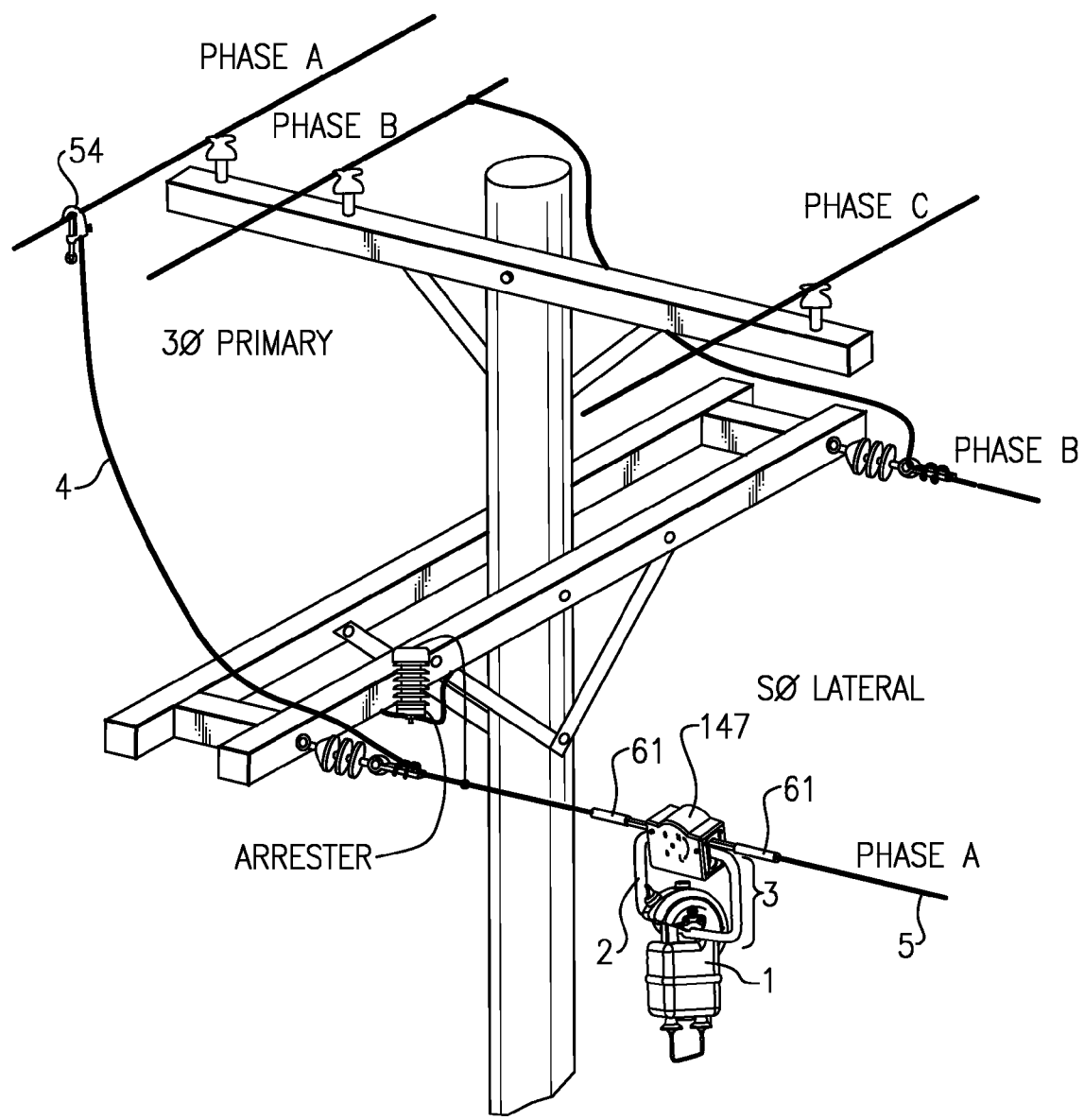
FIG. 23 illustrates a double dead ended LTPS installed on phase A for measuring current in phase A for the delta connected electric power system.

The current continues to flow from both the left tap selector contact fingers 100 and 102 into the fully engaged rotary tap selector blade 86. From the rotary tap selector blade 86 the current flows through the tap selector rotating contact 87 and then through the stationary disc contact 89. In FIG. 13, the bottom of the stationary disc contact includes the hole 93 through which is connected the offset electrically conducting connector 106 which is attached to the stationary disc contact 89 with a bolt 104 and a nut 105. A wire lead 107 is connected from the connector 106 to the connector 30, which is attached to the right anchor rod 63 using the threaded stud 13. So the current then flows from the stationary disc contact 89, through the connector 106, the wire lead 107, the connector 30, and the right anchor rod 63 and to the conductor 5. When the rotary tap selector blade 86 engages the left tap selector contact fingers 100 and 102, the two turns of the winding of wire 6 provide a high threshold current of 17 amperes, as shown in FIG. 23.

As shown in FIG. 4, when the operator handle 72 is pulled "down" the by-pass switch is open, the rotary tap selector blade 86 engages the right tap selector contact fingers 111 and 113. FIGS. 7 and 8 illustrate that the power line current flows from the conductor 4 into the left anchor rod 62 and then to the connector 9 of which the beginning of the winding 8 is attached. This time the current flows through five turns of the winding of wire 6 as shown in FIG. 4.

To accomplish this, the end turn 96 of the two turns of winding of wire 6 enters the "tee tap" 97, but continues through the lower portion of the "tee tap" 97 to the left, as shown in FIG. 8, rather than being tapped off through the wire lead 98. Also, see FIG. 4. The winding leaves the "tee tap" 97 and onto a first turn 108 where three more turns of the winding of wire 6 are made through the loop tube 2 for a total of five turns.

To simplify the FIGS. 7, 8, 10, and 13, it should be noted that only wiring connections to the winding are shown not the five turns of the winding of wire 6 inside the loop tube 2. The end of the fifth turn 109 terminates into a wiring connector 110 shown in FIG. 13. The rotary tap selector blade 86 is rotated to the left in FIG. 13 and is in full engagement with the right tap selector contact fingers 111 and 113 of FIG. 11. The current now flows through five turns, out of the end of the winding at 109, and to the wiring connector 110. The wiring connector 110 is attached to the outside of the back right tap selector contact finger 111. One half of the current flows through contact finger 111 and onto the rotary tap selector blade 86 and the other half of the current flows through the electrically conducting spacer 112 between the right tap selector contact fingers 111 and 113 and then to the inside front right tap selector contact finger 113. From here each half of the current joins together and flows to the rotary tap selector blade 86. The current cannot enter the right anchor rod 63 at this point, because the electrically insulating spacer 114 is located between the back of the back contact finger 113 and the anchor rod 63, as shown in FIG. 9. From the rotary tap selector blade 86 the current continues through the tap selector rotating contact 87, the stationary disc contact 89, and then through the connector 106, the wire lead 107, the connector 30, and the right anchor rod 63 to the electric power line conductor 5 of FIG. 13. When the rotary tap selector blade 86 is fully engaged with the right tap selector contact fingers 111 and 113 the low threshold current of 6.8 amperes is achieved.

Figure 14B:
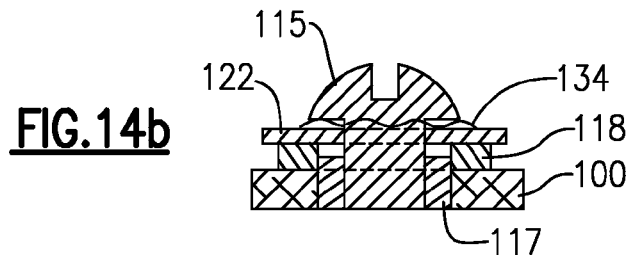
Figure 14A:
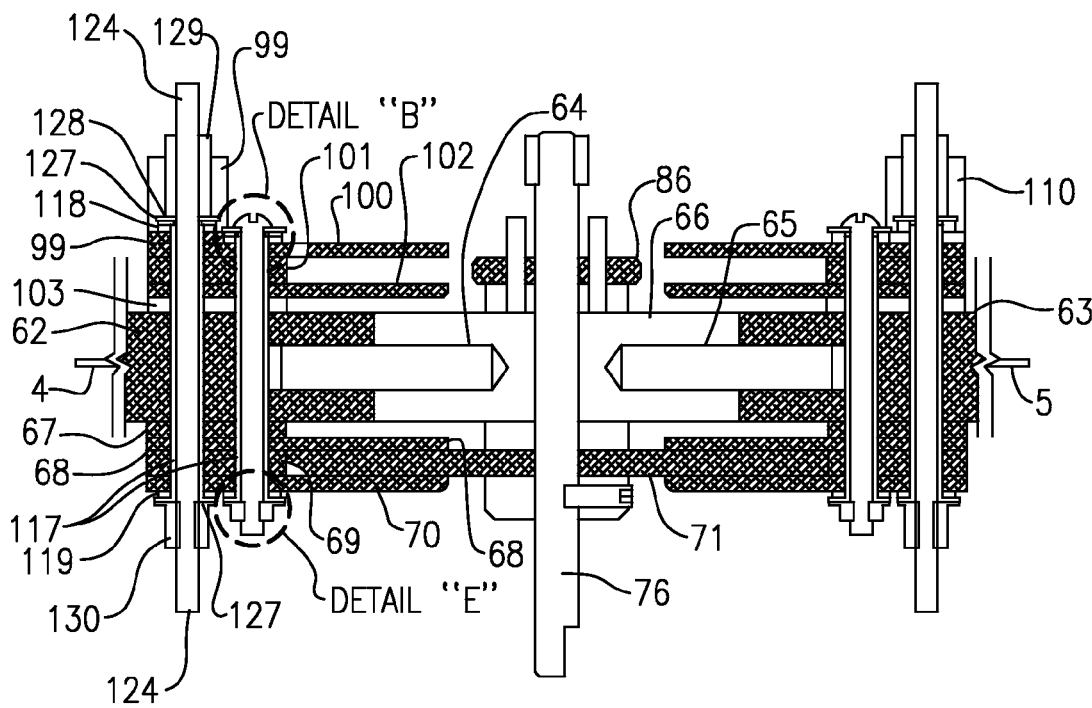
FIG. 14a illustrates a cross-sectional view of contact fingers taken along line E-E of FIG. 7.
Figure 14C:
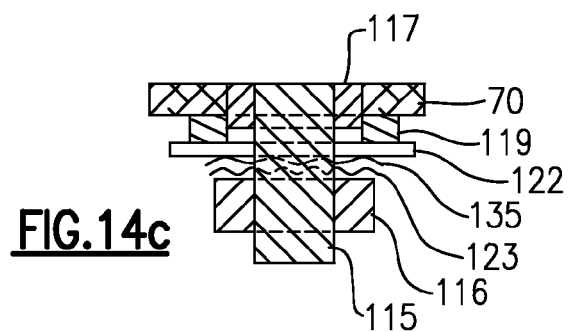
Figure 15:
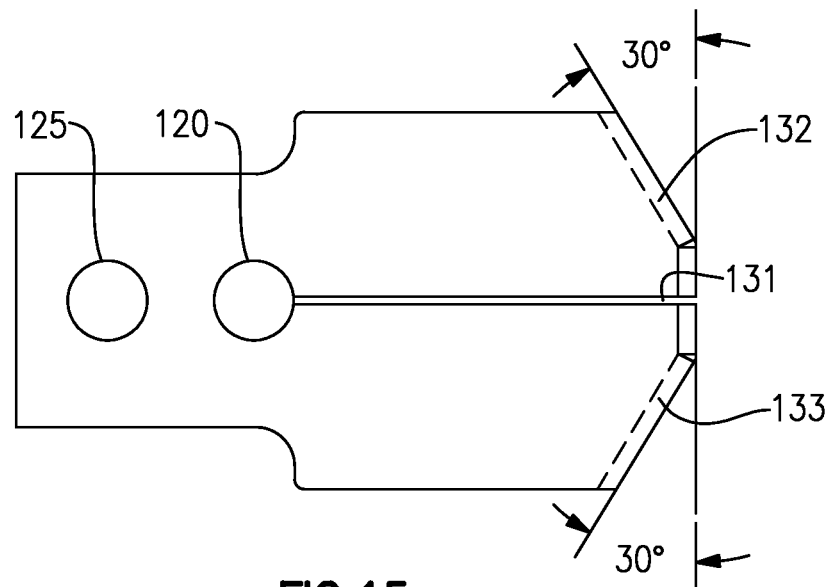
FIG. 15 illustrates an electrically conductive contact finger.

FIGS. 14*a*-14*c* illustrate the contact fingers 68, 70, 100, and 102, the rotary tap selector blade 86, and the rotary by-pass switch blade 71. Since the elements on the left are identical to the elements on the right in FIG. 14*a*, only those elements on the left will be described. The elements which are shaded are electrically conductive. The contact fingers 68, 70, 100 and 102 are mounted on the left and right anchor rods 62 and 63 using a threaded bolt 115 and a nut 116, as shown in FIGS. 14b and 14c, which fits through a hole 120 in the contact finger as shown in FIG. 15.

The by-pass switch contact fingers 68 and 70 and the finger spacer 69 are electrically insulated from the left tap selector contact fingers 100 and 102 and the finger spacer 101 of FIG. 14a. This is achieved by placing an electrically insulating spool 117 and electrically insulating washers 118 and 119 over spool 117 on each end of the spool 117 of FIGS. 14b and 14c. The spool 117 and the washer 118 and 119 are installed over bolt 115, which is inserted into the hole 120 of the contact fingers 68, 70, 100, 102, 111, and 113 and a hole 121 (see FIG. 16) of each of the finger spacers 69 and 101.

The left tap selector contact fingers 100 and 102 and the finger spacer 101 are electrically insulated from the left anchor rod 62 using the insulating spacer 103. The by-pass switch contact fingers 68 and 70 and the finger spacer 69 are electrically attached to the left anchor rod 62 using the electrically conducting spacer 67.

The completed assembly of the bolt 115, the insulating spool 117, the insulating washers 118 and 119, a flat washer 122, a star washer 123, and the nut 116 attached to the left anchor rod 62 is shown in FIG. 14.

Figure 16:
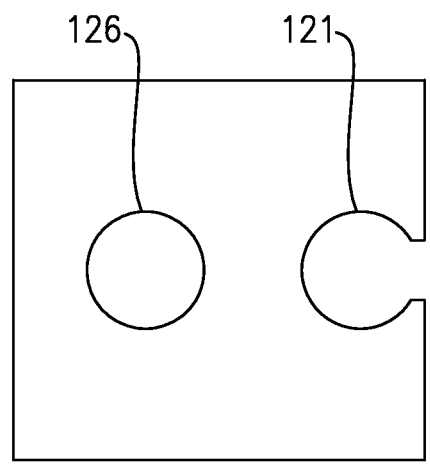
FIG. 16 illustrates an electrically conductive finger spacer.

The insulating spool 117 and the insulating washers 118 and 119 are placed over a threaded stud 124 and inserted into the contact finger holes 125 and electrically conducting finger spacer holes 126 of FIGS. 15 and 16, respectively. However, in this case, the assembly includes the wiring connector 99 which is in electrical contact with the left back tap selector contact finger 100 of FIG. 14. The threaded stud 124 holds the left tap selector contact fingers 100 and 102 and wiring connector 99 to the left anchor rod 62 through the use of a flat washer 127, a star washers 128, a long standoff 129, and a short standoff 130 which are threaded onto each end of the threaded stud 124.

Referring to FIG. 15, the eight electrically conducting contact fingers 68, 70, 100, 102, 111, and 113 on the by-pass switch 140 and tap selector switch 148 are identical. Each contact finger 68, 70, 100, 102, 111, and 113 includes top and bottom leading edges cut at a 30° angle and rounded on the inside edges 132 and 133 to minimize the wear on the rotary by-pass switch blade 71 and the rotary tap selector blade 86.

The rotary by-pass switch blade 71 and the rotary tap selector blade 86 are rounded on the top and bottom edges and on both ends in the case of the rotary by-pass switch blade 71, so that when the blades 71 and 86 are rotated and first contact the inside edges of both sandwiched contact fingers 68, 70, 100, 102, 111, and 113, the contact fingers 68, 70, 100, 102, 111, and 113 are easily and slightly pushed apart. The pressure on the contact fingers 68, 70, 100, 102, 111, and 113 is controlled by wave washers 134 and 135, of FIGS. 14b and 14c. The wave washers 134 and 135 are placed below the head of the bolt 115 in FIG. 14b and above the nut 116 in FIG. 14c.

A slot 131 of FIG. 15 is cut through the middle of the contact fingers 68, 70, 100, 102, 111, and 113 in a horizontal direction and ends at the right side of the first hole 120. The slot 131 makes the contact fingers 68, 70, 100, 102, 111, and 113 more flexible which lowers the required connection shaft 76 torque to push the contact fingers 68, 70, 100, 102, 111, and 113 apart. The hole 120 is located at the end of the slot 131 to prevent fatigue cracking between the first hole 120 and the second hole 125.

As discussed earlier, the two turn winding of the switchable LTPS 147 does not have to be the same wire size as the remaining three turns. As illustrated in FIG. 3 with the rotary tap selector blade 86 engaging the left tap selector contact fingers 100 and 102, current only flows through the two turn winding which has a threshold current of 17 amperes. The maximum current at the high end of the range is limited to 366 amperes with a 2 turn winding of No. 2 copper. In this case, the worst case condition results in a loop tube surface temperature of 150° C.

However, if the two turn winding is replaced with a larger conductor size, for example 1/0 copper, then the maximum current at the high end of the range can be 413 A since this level of current does not cause the loop tube 2 surface temperature to exceed 150° C. With the selection of a larger wire size for the two turn winding there is better utilization of the STR unit 1 rating capacity of 1000 amperes, since 413 amperes×2 turns results in a maximum current as seen by the STR unit 1 of 826 amperes. When the wire size of the two turn winding was the same as the remaining three turns of winding then the maximum current as seen by the STR unit 1 was only 732 amperes (i.e. 366 A×2 turns=732 A). With the larger wire size for the two turn winding of 1/0 copper the power line current can now be increased to 413 amperes and as low as 6.8 amperes for the five turns. This new dynamic range of 60.7 times (i.e. 413 A÷6.8 A=60.7 times) is 2.07 times better than the fixed tap five turn (i.e. 60.7÷29.4=2.07 times). Other suitable wire sizes, number of turns and more taps can be added to fit the range of power line current requirements of any specific application.

The 1/0 copper two turn winding and the No,. 2 AWG copper for the three turn winding are easily adaptable to the design of FIGS. 7-8 by just changing the wire size from the beginning of the first turn 8 of the connector 9 to the end turn 96 of the "tee tap" 97 to 1/0 copper.

Figure 17:
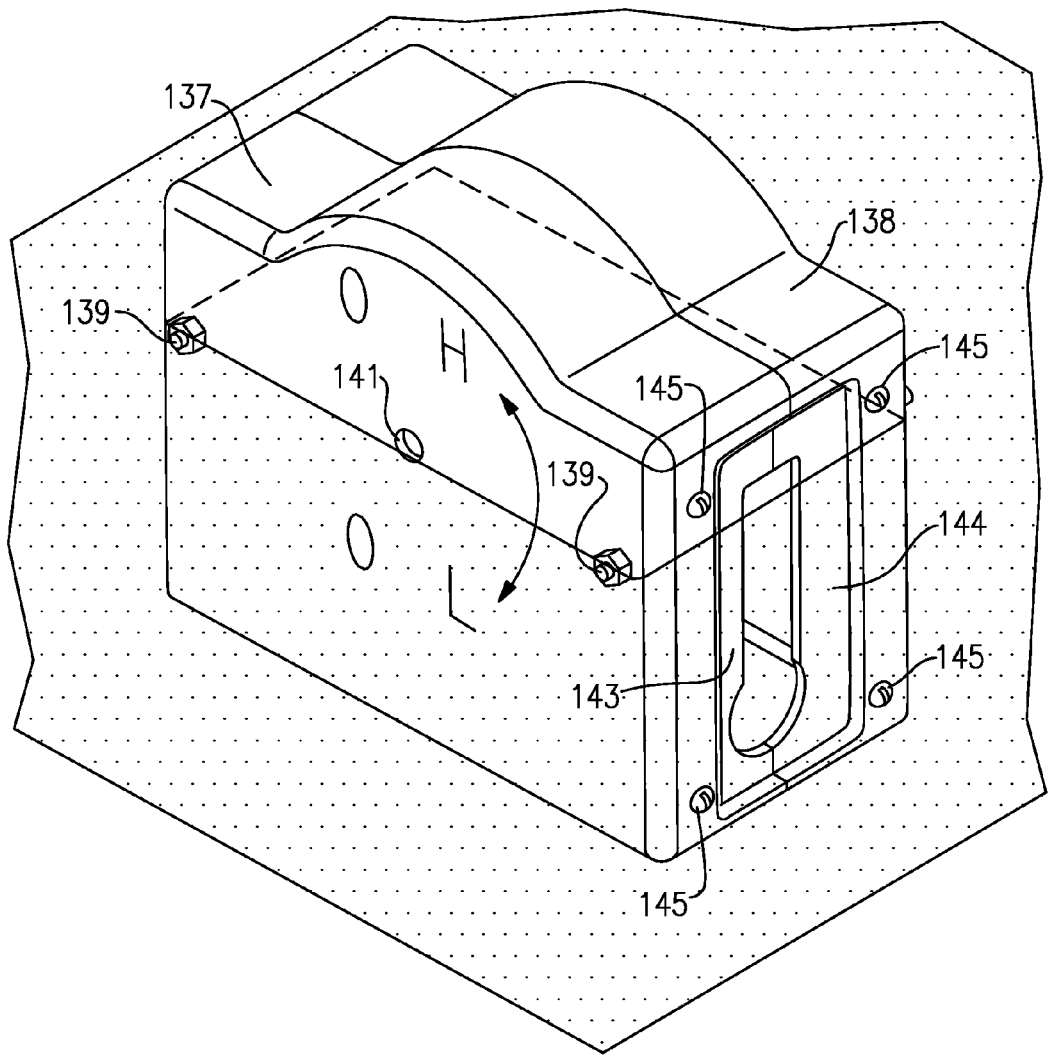
FIG. 17 illustrates a cover for the tap selector switch and the by-pass switch.
Figure 18:
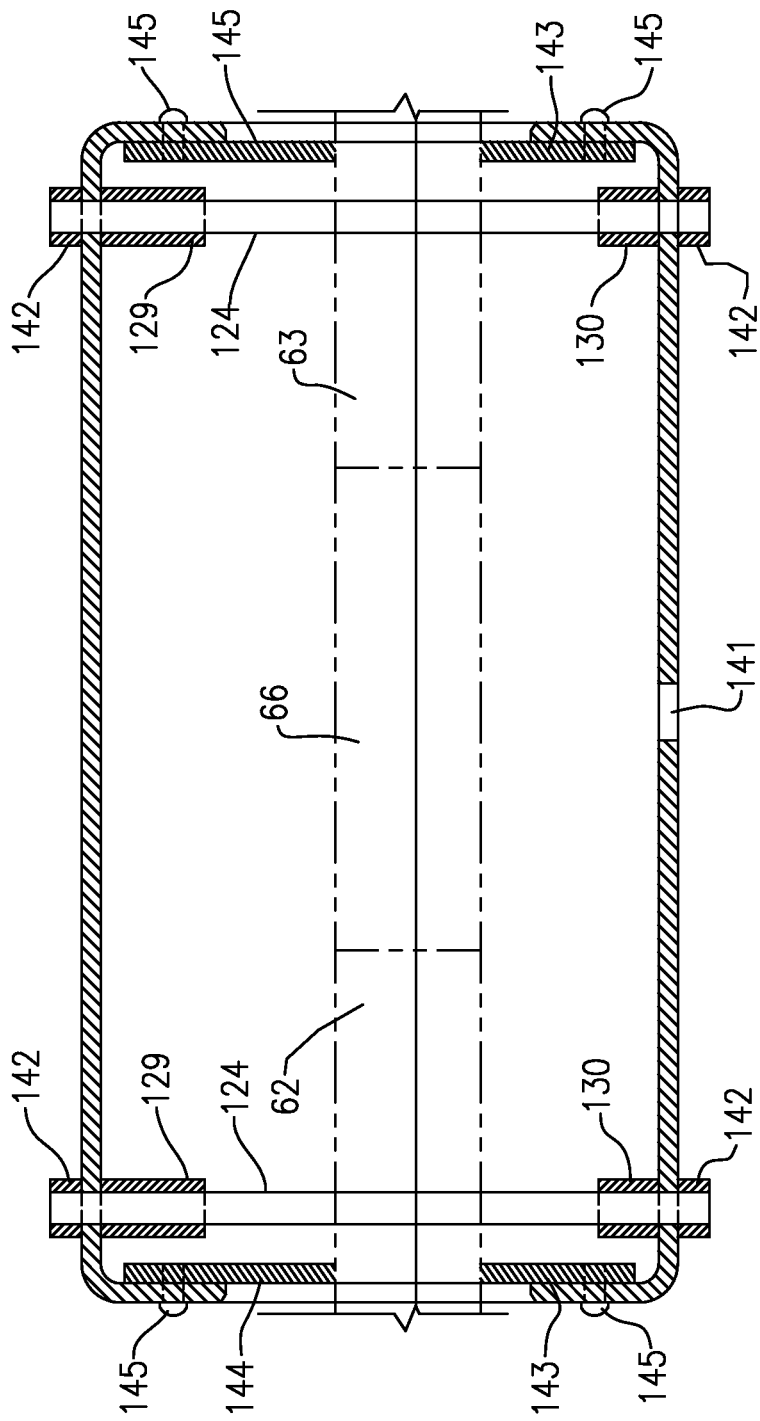
FIG. 18 illustrates a cross-section view of the cover taken along plane F of FIG. 17.

The cover for the tap selector switch 148 and by-pass switch 140 includes two casting halves 137 and 138 and two sets of inserts as illustrated in FIG. 17. The casting halves 137 and 138 which are attached to the left and right anchor rods 62 and 63 using the threaded studs 124 of FIG. 14a-14c. Each of the casting halves 137 and 138 is held onto the threaded studs 124 using lock nuts 142 as shown in FIG. 18.

The front casting half 137 has a central hole 141 which is fitted over the connection shaft 76, after which the operator handle hub 75 and the operator handle 72 are installed. As noted earlier, the threaded studs 124 are electrically insulated from the contact fingers 68, 70, 100, 102, 111, and 113 and left and right anchor rods 63 and 63. Therefore when the castings halves 137 and 138 are installed on the threaded studs 124, the castings halves 137 and 138 do not become a part of the current path from the conductor 4 to the conductor 5.

Furthermore, the left and right insulating inserts 143 and 144 are attached to the casting halves 137 and 138 using four screws 145. The same arrangement of inserts 143 and 144 and screws 145 are installed on the opposite end. The lettering on the front casting half 137 mimics the position of the operator handle 72. When the operator handle 72 is pointing to the right, the by-pass switch is closed as indicated by the "C" on the casting half 137. When the operator handle 72 is pushed up the switchable LTPS 147 is in the high "H" position for high threshold current and "0" indicating the by-pass switch is "open". When pulled down the operator handle 72 points to the low "L" position, meaning low threshold current, and the "0" indicating the by-pass switch is "open".

The switchable LTPS 147 is designed to allow the removal of the loop tube assembly 3, while the switchable LTPS 147 remains installed. First, before the loop tube assembly 3 is removed the by-pass switch must be closed. The nut 105 and bolt 104 of the offset connector 106 are removed as shown in FIG. 13. Next, set screws 146 are loosened on the wiring connectors 99 and 110 and leads 109 and 98 are pulled down therefrom. The final step is to take off the nuts 17 from the two threaded studs 13 of FIG. 11, and the loop tube assembly 3 will drop down from the left and right anchor rods 62 and 63.

FIG. 19 illustrates a jumper J1 from the tap point on phase A of the three phase (3Ø) primary to the tap point on the phase A of the single phase (SØ) lateral. The first installation method shown in FIG. 20 bridges the jumper J1 with the LTPS 147.

Figure 20:
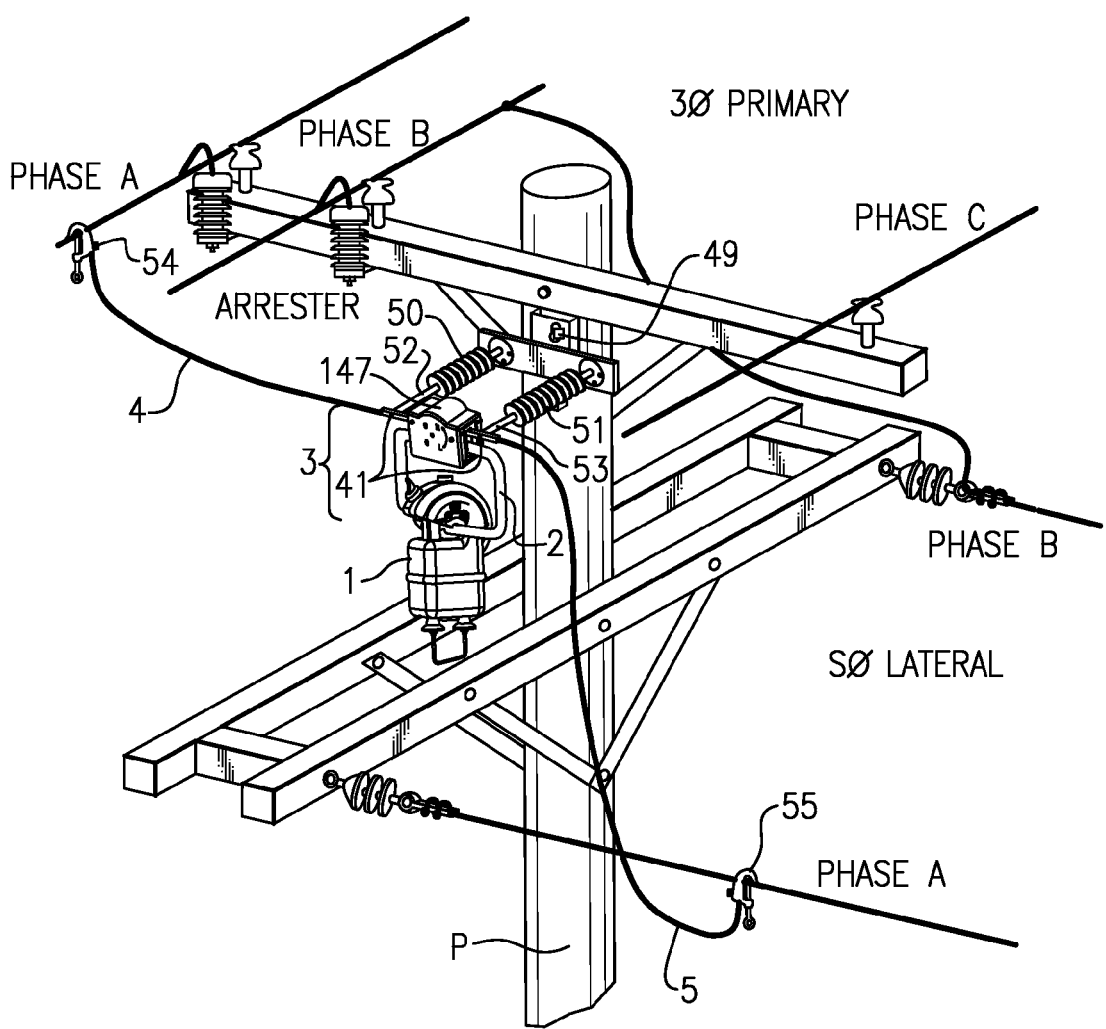
FIG. 20 illustrates the LTPS suspended from a pole mounted bracket for measuring current of phase A for the delta connected electric power system.

FIG. 20 illustrates a pole mounted cantilevered insulator method of installing the LTPS 147 for a delta connected electric power system. The installation method of FIG. 20 is especially suitable for small power line conductors (such as No. 6 AWG copper) where the weight of the STR unit 1 and LTPS 147 may cause concern for old construction where the copper conductor is fully annealed. A pole mounted bracket 49 includes two horizontal spaced apart cantilevered insulators 50 and 51, which are attached to the pole mounted bracket 49, installed at the top of the utility pole P. Two end caps 52 and 53 on the ends of the insulators 50 and 51 have the same diameter as holes 41 of FIG. 11 in the left and right anchor rods 62 and 63. The holes 41 in the left and right anchor rods 62 and 63 are spaced the same distance apart as the two cantilevered insulators 50 and 51.

The LTPS 147 is installed on the two end caps 52 and 53, which have holes drilled at the outside extremity for cotter pins. Once the LTPS 147 is in place, the cotter pins are inserted into the holes to prevent the left and right anchor rods 62 and 63 from sliding off the end caps 52 and 53. The jumper J1 of FIG. 19 remains in place with one end attached to phase A of the 3Ø primary and the other end attached to phase A of the SØ lateral. Therefore, there is no interruption of service to customers fed off of phase A of the SØ lateral.

Next the conductor 4 of the LTPS 147 of FIG. 20 is attached using a hotstick to phase A of the 3Ø primary with a hot line clamp 54 and the conductor 5 of the LTPS 147 is attached using a hotstick to phase A with a hot line clamp 55 to phase A of the SØ lateral. The jumper J1 is then removed, and current now flows through the LTPS 147 without a service interruption. The STR unit 1 is then installed on the loop tube 2 of the LTPS 147. Once the STR unit 1 is installed on the LTPS 147, the current traveling through the turns of wires 6 generate power for the power supply transformer PST of the STR unit 1. The power generated from the power supply transformer is sent to a power supply module 151 to power onboard electronics module 152, a transmitter/receiver 153, and an antenna 81 (see FIG. 1) and begins to transmit data with the transmitter/receiver 153 and the antenna 81.

Figure 21:
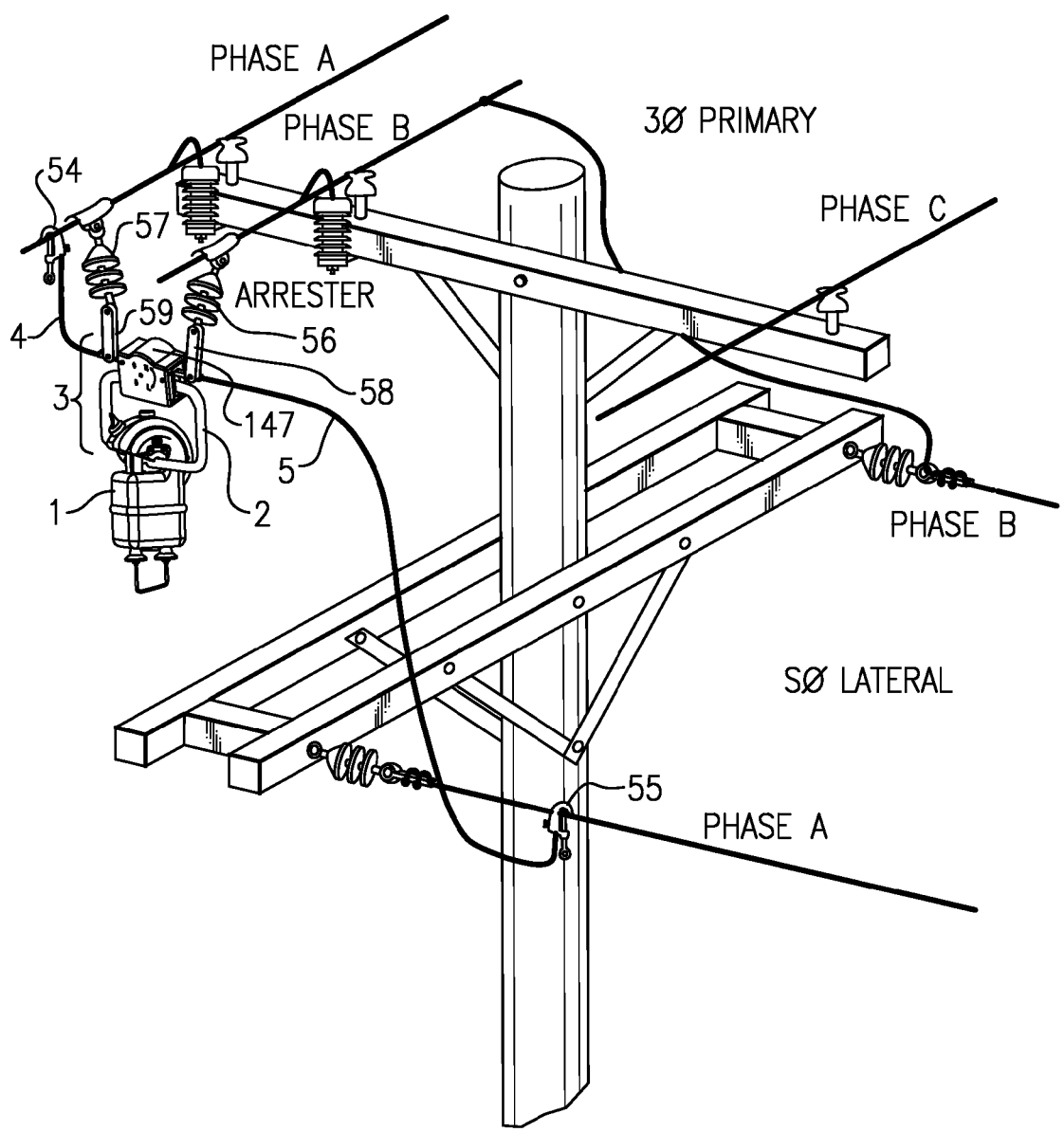
FIG. 21 illustrates the LTPS suspended from phase A and phase B conductors with suspension insulators for measuring current in phase A for the delta connected electric power system.

FIG. 21 illustrates a second method of installation using two suspension insulators 56 and 57 mounted on phase A and phase B of the delta connected system. Links 58 and 59 are attached to the suspension insulators 56 and 57 on one end, and the pins 40 are inserted through bottom end holes of the links 58 and 59 and through the left and right anchor rods 62 and 63. Cotter pins are installed in holes 60 (see FIG. 9) in the pins 40 shown in FIG. 9 to hold the left and right anchor rods 62 and 63 to the links 58 and 59. With the original jumper J1 of FIG. 19 in place, insuring no interruption of service, the conductor 4 is attached to phase A of the 3Ø primary using a hotstick and the hot line clamp 54. Similarly, the conductor 5 is attached to phase A of the SØ lateral using the hotstick and the hot line clamp 55, the original jumper J1 of FIG. 19 is then removed, and current now flows from phase A of the 3Ø primary to the phase A of the SØ lateral through the winding of wire 6 of the LTPS 147. The STR unit 1 is then installed on the loop tube 2 of the LTPS 147 and as before transmits data.

Figure 22:
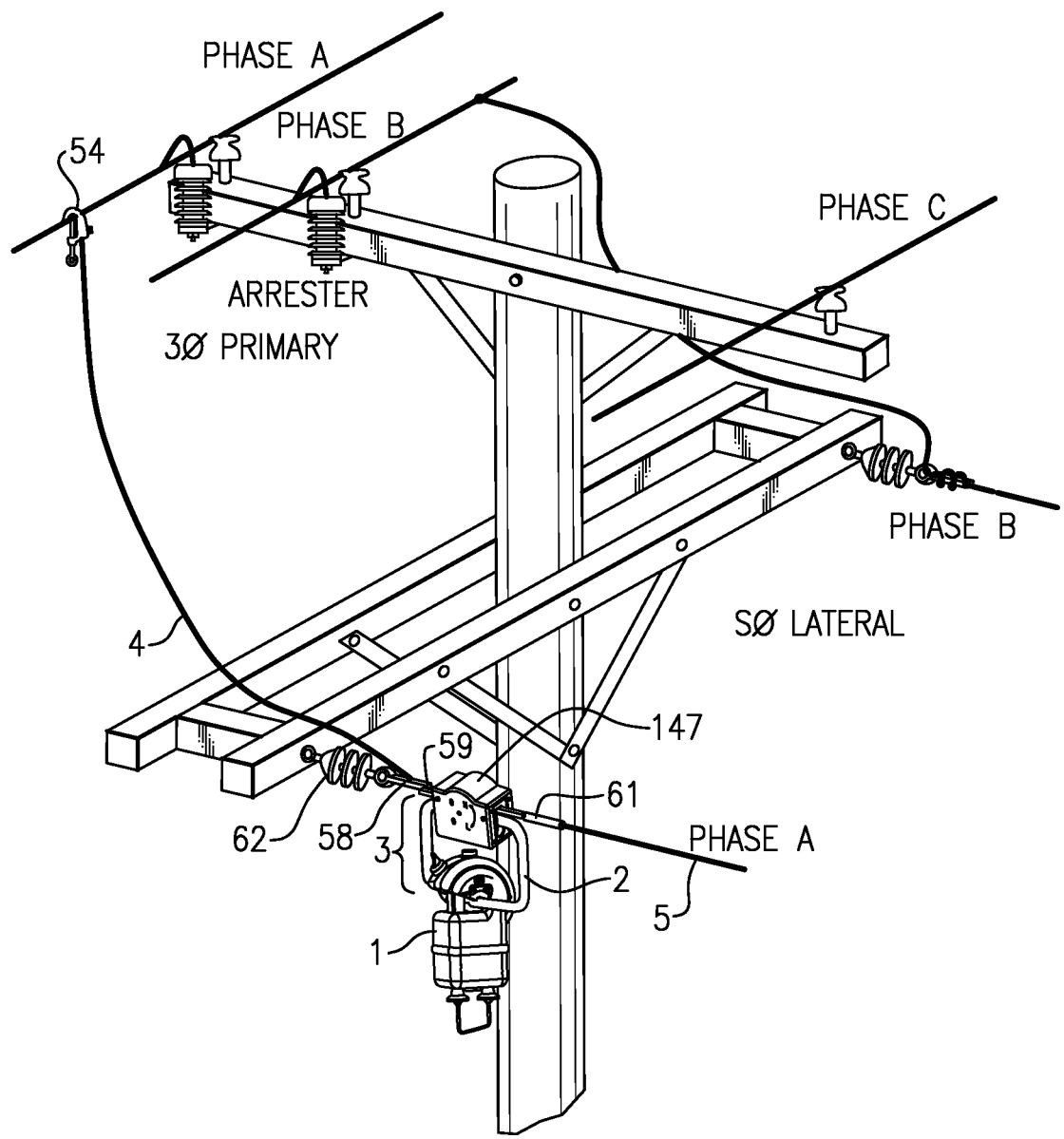
FIG. 22 illustrates a single dead ended LTPS installed on phase A for measuring current in phase A for the delta connected electric power system.

FIG. 22 illustrates a third method of installation using an automatic dead end 61 shown in FIG. 1 on the right side of the loop tube 2 and the links 58 and 59 of FIG. 21 on the left side for the delta connected system. The automatic dead end 61 is a commercially available product which allows the power line conductor 5 to be inserted into spring loaded jaws internal to the device upon which applying tension to the power line conductor 5 automatically grips the power line conductor.

The left end of the automatic dead end 61 is formed into a "U" bracket with a hole in the end which fits onto the right anchor rod 63 using pin 40 and cotter pin. The end of the conductor 5 is then inserted into the hole in the end of the right anchor rod 63 and held electrically in contact with same using the two set screws 12 of FIG. 9. The left anchor rod 62 is attached to the two links 58 and 59 using pin 40 and cotter pin, and the left ends of the links 58 and 59 are attached to a dead end insulator 62 using pin 40 and cotter pin. Here again the original jumper J1 of FIG. 19 remains in place while the LTPS 147 is being installed. As before, conductor 4 is tapped to phase A of the 3Ø primary using hot line clamp 54, the original jumper J1 is removed, and then the STR unit 1 is installed using a hot stick on the loop tube 2.

FIG. 23 illustrates a fourth method of installation similar to the method shown in FIG. 22, except two automatic dead ends 61 are used as in FIG. 1. The same process of installing the automatic dead end 61 of the third method shown in FIG. 22 is applied to both the left anchor rod 62 and the right anchor rod 63. Again the original jumper J1 as shown in FIG. 19 remains connected until the hot line clamp 54 and conductor 4 are installed.

Figure 24:
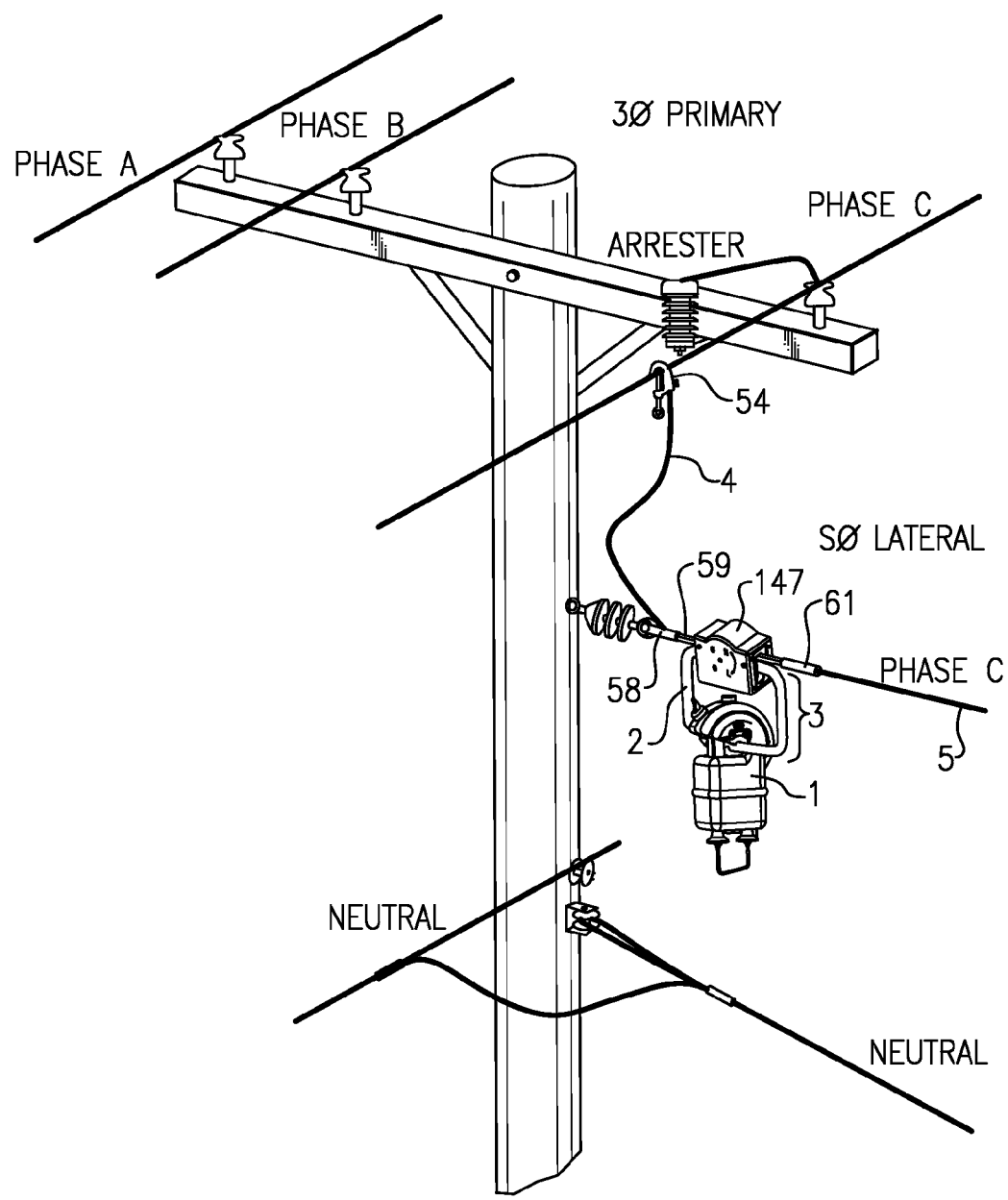
FIG. 24 illustrates a single dead ended LTPS installed on phase C for measuring current in phase C for wye connected electric power system.

FIG. 24 illustrates a fifth method of installation which is similar to the method shown in FIG. 22 except it is applied to a wye connected electric power system with the phase C current being measured on the SØ lateral.

Figure 25:
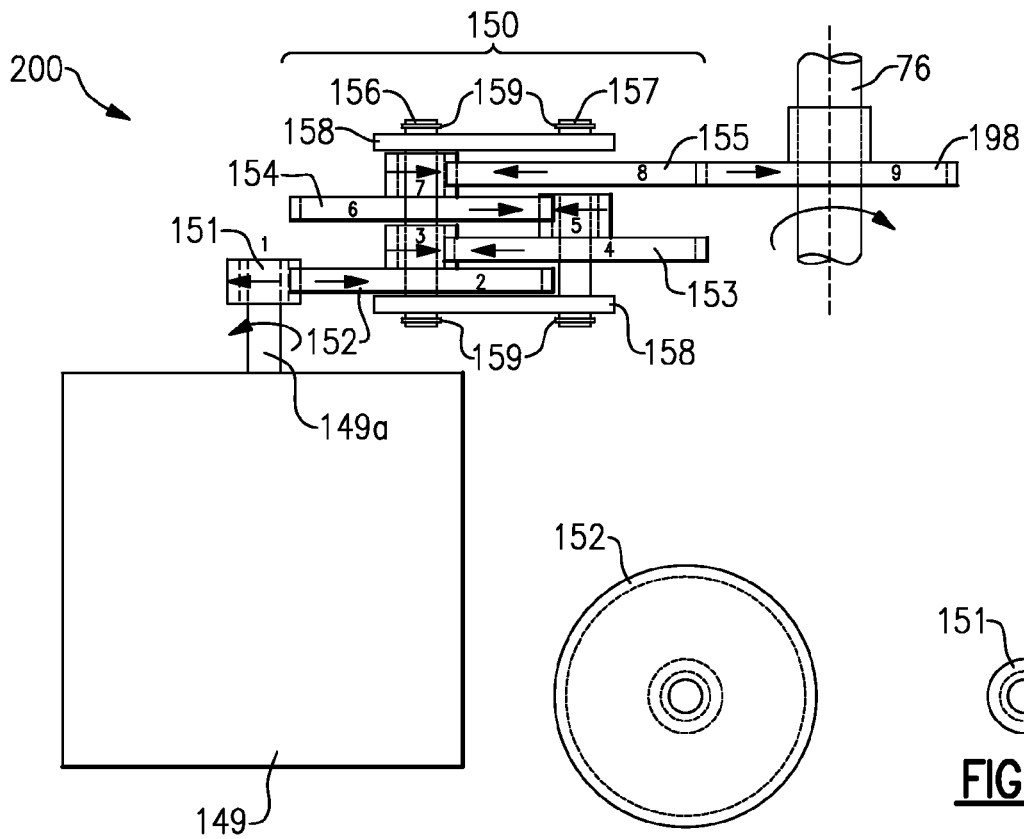
FIG. 25 illustrates a top view of a gear train and a motor drive for rotating a connection shaft for an automatic LTPS.
Figure 26:
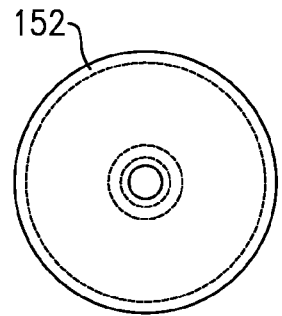
FIG. 26 illustrates a front view of a large combination gear with 60 teeth.
Figure 27:
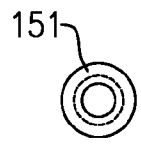
FIG. 27 illustrates a front view of a small gear with 12 teeth.
Figure 28:
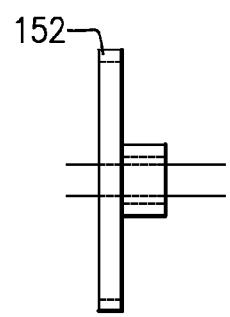
FIG. 28 illustrates an end view of the large combination gear of FIG. 26 mounted on a shaft.
Figure 29:
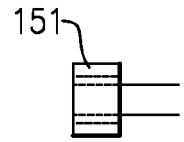
FIG. 29 illustrates an end view of the small gear of FIG. 27 located on a shaft.

FIG. 25 illustrates an automatic low threshold current power supply ("LTPS") 200. The automatic LTPS 200 is similar to the LTPS 147 except where shown in the Figure or discussed below. The LTPS 200 is made by removing the operator handle 72 from the connecting shaft 76. The rotating bushing 81 of FIG. 9 is replaced with a toothed gear 198 shown in FIG. 25. The toothed gear 198 is attached to the connecting shaft 76, which is rotated clockwise or counterclockwise with an AC reversible motor 149 and a gear train 150.

FIG. 25 shows the AC reversible motor 149, the gear train 150, and the toothed gear 198 interconnected. The AC reversible motor 149 has a small 12 tooth drive gear 151 mounted on its output shaft 149a. The drive gear 151 drives a combination gear 152 having a large gear of 60 teeth and a small gear of 12 teeth that are physically connected together as one rotating gear. When the drive gear 151 rotates counterclockwise, the combination gear 152 turns clockwise as indicated by the arrows.

The combination gear 152 drives a second combination gear 153 and the second combination gear drives a third combination gear 154. The combination gear 154 drives a large gear 155 of 60 teeth which in turn is geared to the connecting shaft toothed gear 198 having 60 teeth. The combination gears 152 and 154 are free to turn and are mounted on an axle 156. The combination gear 153 and the large gear 155 are free to turn and are mounted on an axle 157. The axles 156 and 157 are mounted to a frame 158 and each axle 156 and 157 is held in place through holes in the frame 158 and retaining rings 159 installed on ends of the axles 156 and 157. Since the gear ratio for each set of gears is five (i.e. 60÷12=5) and there are 4 sets, then the resultant gear ratio for the train 150 is 625, or (5)(5)(5)(5).

Figure 30:
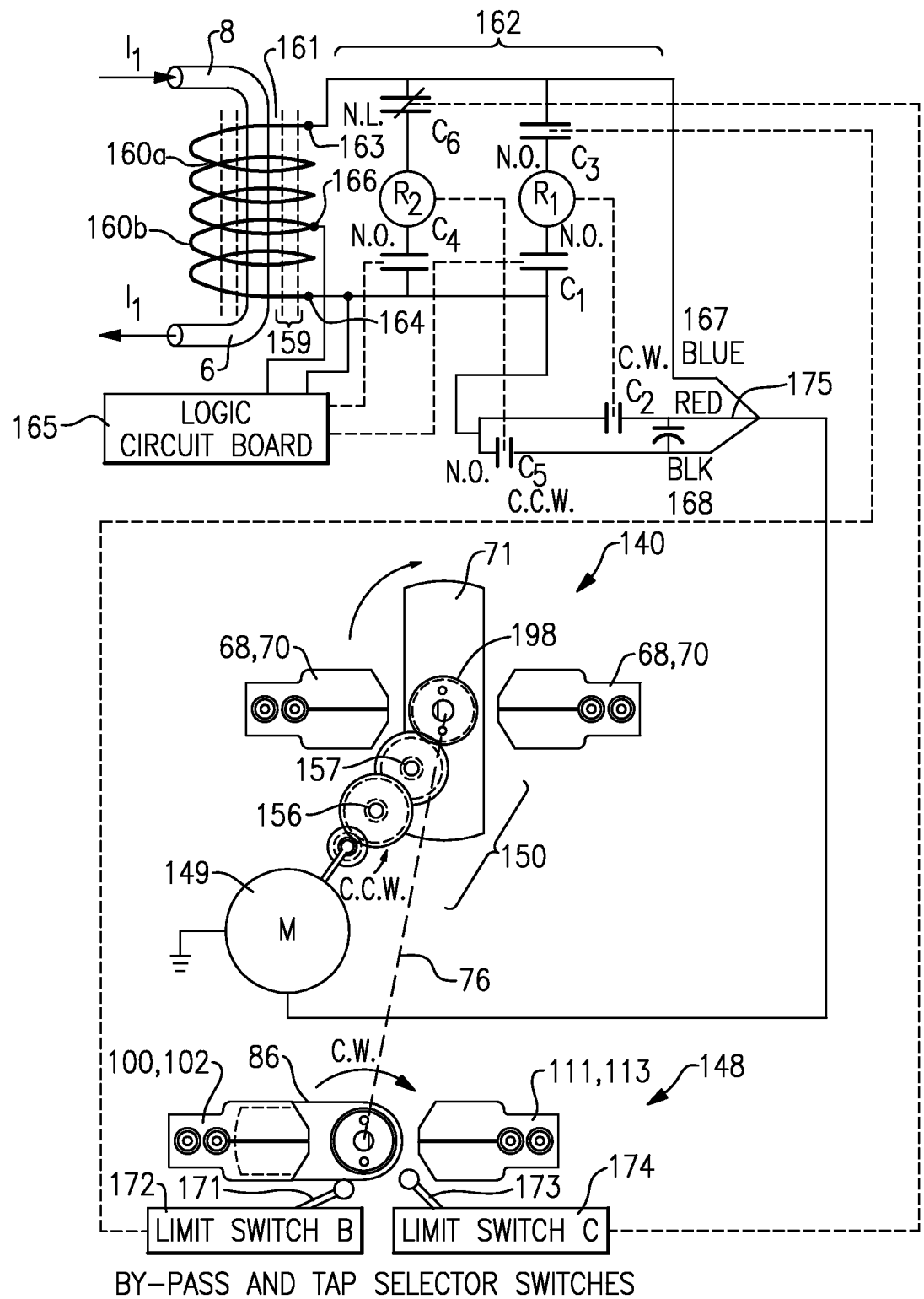
FIG. 30 illustrates a motor control diagram for the automatic LTPS.

The power supply and motor control circuit 162 are shown in FIG. 30. The power supply transformer 160*a* includes an iron donut shaped core 159 with a toroid coil of wire 160*b* wound on the iron donut shaped core 159. The power supply transformer 160*a* has a vertical hole 161 in the center of the donut shaped core 159 of which the first turn 8 of the winding of wire 6 shown in FIG. 30 is inserted. The power line primary current $I_1$ flows through the winding of wire 6 beginning at the first turn 8 of FIG. 30 and proceeds vertically downward through the vertical hole 161. The power to the motor control circuit 162 and ultimately the power to the motor 149 is fed from the secondary of winding 160*b* through terminals 163 and 164. A logic circuit board 165 receives power from the reduced voltage tap on winding 160*b* at terminals 166 and 164.

Figure 31:
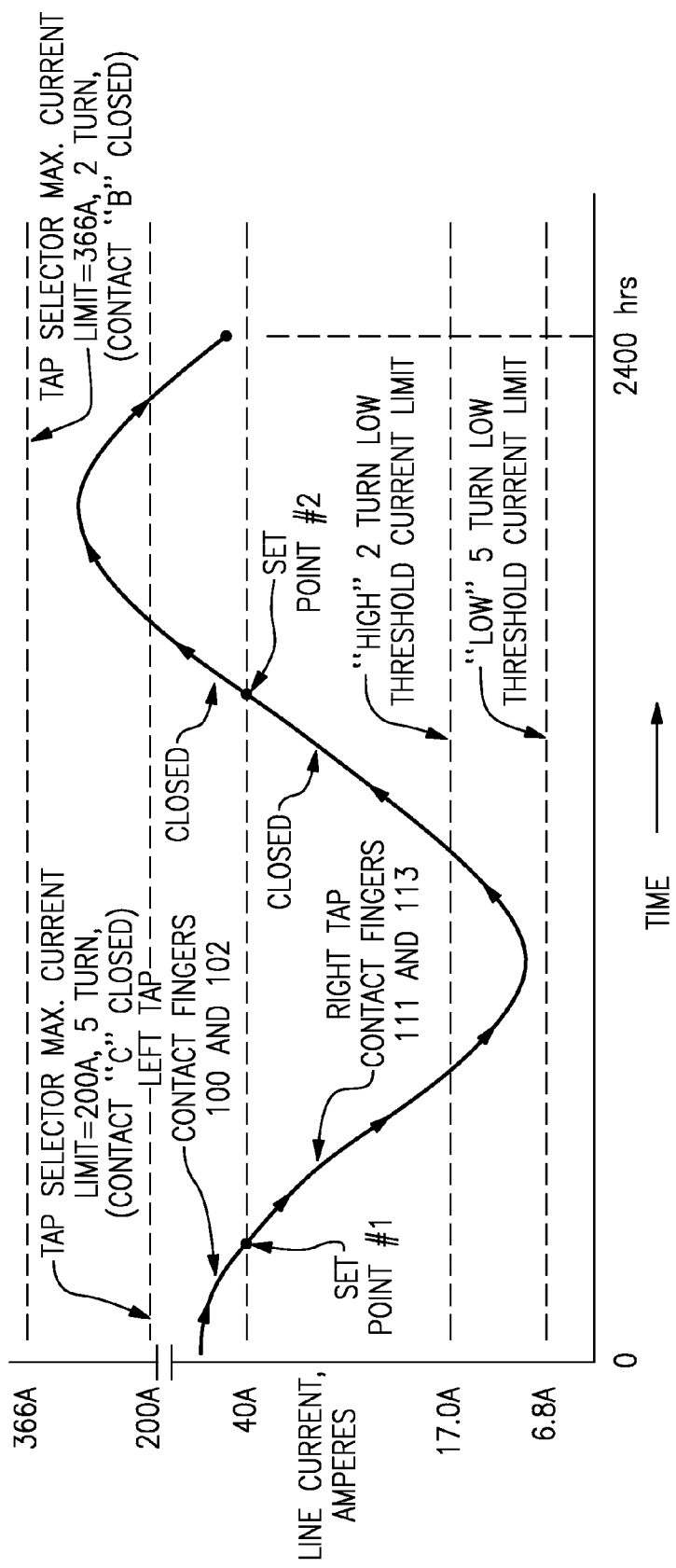
FIG. 31 illustrates a line current variation throughout a 24 hour day and the automatic LTPS switching from high to low and back to high.

An example operation of the logic circuit board 165 and the motor control circuit 162 is shown in FIG. 31. In this example, the power line load current magnitude varies throughout a 24 hour period as shown by the trace with the arrows in FIG. 31. At time equals zero, the load current is above 40 amperes and the rotary tap selector blade 86 remains engaged with the left tap selector contact fingers 100 and 102 as shown in FIG. 30. Therefore, two turns of the winding of wire 6 are in the circuit and the "high" threshold current is 17 amperes on its primary. If the line current were to drop down below 17 amperes then the STR unit 1 would not operate with full transmit power, since the STR unit 1 power supply needs 34 amperes on its primary.

To prevent the STR unit 1 from not operating at full transmit power, the current I from the power line conductors 4 and 5 being monitored by the logic circuit board 165 measures the secondary current $I_2$ of the power supply transformer 160*a* flowing from terminal 166 to terminal 164 as shown in FIG. 30. Since the turns ratio of the power supply transformer 160*a* is known, then the logic circuit board 165 knows the value of the primary line current $I_1$. Once the logic circuit board 165 senses a value of primary current of 40 amperes which is the set point #1 given in FIG. 31, and the current is decreasing in magnitude, then the logic circuit board 165 signals the closure of the normally open (N.O.) contact $C_4$.

Since contact $C_6$ is normally closed (N.C.), a full secondary voltage appears across the terminals 163 and 164 when the contact $C_4$ is closed. When the contact $C_4$ closes, a relay coil $R_2$ becomes energized and closes a normally open (N.O.) contact $C_5$. With the contact $C_5$ closed, the full secondary voltage is applied across the input terminals 167 (blue) and 168 (black) of the motor 149 and causes the motor shaft 149*a* to rotate counterclockwise.

As shown in in FIG. 25, when the connecting shaft 76 of the gear train 150 begins to rotate clockwise, the rotary tap selector blade 86 of FIG. 30 starts to rotate clockwise toward the right tap selector contact fingers 111 and 113. As the rotary tap selector blade 86 leaves contact with the left tap selector contact fingers 100 and 102, a rocker arm 171 of limit switch B 172 flips up (like that shown for limit switch C 173) and closes the contact $C_3$.

When the rotary tap selector blade 86 is fully engaged with the right tap selector contact fingers 111 and 113 the rocker arm 173 of the limit switch C 174 is pushed down by the rotary tap selector blade 86 which opens the normally closed (N.C.) contact $C_6$ and interrupts power to the motor 149, which stops further rotation of rotary tap selector blade 86. The elapse time from contact open on the left tap selector contact fingers to contact close with the right tap selector contact fingers is approximately 12.6 seconds. With the rotary tap selector blade 86 in contact with the right tap selector contact fingers there are now five turns of wire in the circuit and the power line current can drop down to the "low" threshold current of 6.8 amperes as shown in FIG. 31 with the contact $C_3$ closed and the contact $C_6$ open.

As time continues, the power line load current magnitude starts to increase and follow the trace upward until it reaches a set point #2. When the power line current is greater than 40 amperes and increasing, the logic circuit board 165 signals the contact $C_1$ to close. When contact $C_1$ closes, the relay coil $R_1$ is energized with the full secondary voltage appearing across 163 and 164 because the contact $C_1$ and the contact $C_3$ are closed.

When the relay coil $R_1$ caused contact $C_2$ to close full secondary voltage now appears across 175 (red) and 167 (blue), which reverses the rotation of the motor 149. Now the output shaft 149*a* rotates clockwise and the connecting shaft 76 rotates counterclockwise. When the rotary tap selector blade 86 starts to rotate counterclockwise and begins to leave the right tap selector contact fingers 111 and 113, the rocker arm 173 of the limit switch 174 "flips up" and closes the contact $C_6$. When the rotary tap selector blade 86 is fully engaged with the left tap selector contact fingers, the rocker arm 171 of the limit switch B 172 is pushed down which opens the contact $C_3$ and de-energizes the relay coil $R_1$ which in turn opens the contact $C_2$. With the contact $C_2$ open, the power supply from terminals 175 (red) and 167 are open and the motor shaft 149*a* ceases to rotate clockwise. When the rotary tap selector blade 86 is in full contact with the left tap selector contact fingers, then only two turns of the winding of wire 6 are now in the circuit and the power line current can go as high as 366 amperes, even though the trace in FIG. 31 shows the line current is less than 366 amperes at its peak.

As shown in FIG. 30, the operation of the by-pass switch 140 and the tap selector switch 148 is same as that described earlier for LTPS 147.

Furthermore, there is never an interruption of power to customers during any switching operation for the LTPS 200 because either the rotary by-pass blade 71 or the rotary tap selector blade 86 will always be in contact with at least one set of the contact fingers 68, 70; 100, 102; and 111, 113.

When the current in the conductors 4 and 5 drops to a very low level, it is possible that there might not be enough current to power the motor 149, such that the secondary voltage across terminals 163 and 164 of the power supply transformer 158 is consequently very low. In this case the motor 149 may stall out. However, the motor 149 is designed to remain in a stall condition continuously preventing harm to the motor. As a backup, during this same period of time when the power line current is very low, the logic circuit board 165 senses the low voltage condition on terminals 164 and 166 and opens the contacts $C_1$ and $C_4$. Therefore, the relay coils $R_1$ an $R_2$ can never have the low voltage applied across their terminals, and the $R_1$ and $R_2$ relay coils can never "pick up" to close the contacts $C_2$ or $C_5$. With the contacts $C_2$ and $C_5$ open there cannot be a low voltage supply to the motor 149 and it cannot go into a "stall" condition. When an acceptable level of voltage returns then the logic circuit board 165 closes either the contacts $C_4$ or $C_1$ to resume normal operation. In addition, if a power line outage occurs during a switching operation and there are no contact fingers of the tap selector engaged with the tap selector blade 86, then there is no outage to customer load when the power is restored because the by-pass blade 71 will always be engaged with its contact fingers. It should be noted there is never a voltage difference across any blade, whether 86 or 71, and their set of contacts 100, 102, and 111, 113, or 68, and 70. Therefore, there is never any arcing during the switching operation. This prevents the wearing of the contact fingers and their blades.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A method of operating a device connectable to at at least one electric power line conductor comprising the steps of:
attaching the device to a first electric power line conductor;
sensing a current in the first electric power line conductor; and
selecting between a first number of windings and a second number of windings connected in series with the first electric power line conductor by rotating a rotary by-pass switch blade and a rotary tap selector switch blade mounted on a common shaft.

2. The method of claim 1 wherein the device includes an automatic switchable connecting device.

3. The method of claim 2 wherein the automatic switchable connecting device includes the rotary tap selector blade and a first set of contact fingers and a second set of contact fingers.

4. The method of claim 3 wherein the automatic switchable connecting device engages the rotary tap selector blade with the first set of contact fingers in response to a first current profile and the second set of contact fingers in response to a second current profile.

5. The method of claim 4 including selecting the first set of contact fingers when a current level in the first electric power line conductor is low and falls below a first set point.

6. The method of claim 5 wherein the first set point includes a current level having a decreasing rate of change of current measured in the first electric power line conductor.

7. The method of claim 5 wherein selecting the first set of contact fingers directs the current through the first number of windings.

8. The method of claim 7 wherein the first number of windings includes at least two turns.

9. The method of claim 4 including selecting the second set of contact fingers when a current level rises above a second set point.

10. The method of claim 9 wherein the second set point includes a current level having an increasing rate of change of current in the first electric power line conductor.

11. The method of claim 9 wherein selecting the second set of contact fingers directs the current through the second number of windings.

12. The method of claim 11 wherein the second number of windings includes at least three turns.

13. The method of claim 1 wherein a wire diameter of the first number of windings is greater than a wire diameter of the second number of windings.

14. The method of claim 2, wherein the first number of windings includes an electrically conductive insulated first winding of wire wound into at least two turns having a first end and a second end, wherein the first end is configured to be attached to the first electric power line conductor.

15. The method of claim 14, wherein the second number of windings are wound into at least one turn and have a first end connected to the second end of the first number windings and a second end configured to be attached to a second electric power line conductor.

16. The method of claim 15 wherein the automatic switchable connecting device is configured to move between a first position with the first winding of wire in series with the first power line conductor and the second power line conductor in response to a first power line current profile and a second position with the first power line conductor, the first winding of wire, and the second winding of wire connected to the second power line conductor in series in response to a second power line current profile.

17. The method of claim 1, wherein the first electric power line conductor is an exterior utility power line configured to extend between utility poles.

18. The method of claim 15, wherein the second electric power line conductor is an exterior utility power line configured to extend between utility poles.

* * * * *

UNITED STATES PATENT AND TRADEMARK OFFICE
CERTIFICATE OF CORRECTION

| | |
|---|---|
| PATENT NO. | : 9,167,885 B2 |
| APPLICATION NO. | : 14/479410 |
| DATED | : October 27, 2015 |
| INVENTOR(S) | : Murray W. Davis |

Page 1 of 1

It is certified that error appears in the above-identified patent and that said Letters Patent is hereby corrected as shown below:

IN THE CLAIMS:

In claim 15, column 16, line 21; after "number" insert --of--

Signed and Sealed this
Twelfth Day of April, 2016

Michelle K. Lee
*Director of the United States Patent and Trademark Office*